(12) United States Patent
Dority

(10) Patent No.: US 6,374,684 B1
(45) Date of Patent: Apr. 23, 2002

(54) FLUID CONTROL AND PROCESSING SYSTEM

(75) Inventor: Douglas B. Dority, Mill Valley, CA (US)

(73) Assignee: Cepheid, Sunnyvale, CA (US)

( * ) Notice: Subject to any disclaimer, the term of this patent is extended or adjusted under 35 U.S.C. 154(b) by 0 days.

(21) Appl. No.: 09/648,570

(22) Filed: Aug. 25, 2000

(51) Int. Cl.⁷ .................................................. G01N 1/00
(52) U.S. Cl. .................................................... 73/864.81
(58) Field of Search ........................ 73/864.81, 863.23, 73/864.35, 863, 863.72, 863.73; 422/63, 67, 81; 137/625, 625.11, 625.12, 625.17, 625.46, 625.47

(56) References Cited

U.S. PATENT DOCUMENTS

| | | | |
|---|---|---|---|
| 4,231,990 A | * 11/1980 | Jottier | 73/863.33 |
| 4,506,558 A | * 3/1985 | Bakalyar | 73/863.72 |
| 4,726,237 A | * 2/1988 | Yung | 73/863.73 |
| 4,983,523 A | 1/1991 | Li et al. | 435/173 |
| 5,105,851 A | 4/1992 | Fogelman | 137/625.11 |
| 5,143,084 A | 9/1992 | Macemon et al. | 128/771 |
| 5,374,522 A | 12/1994 | Murphy et al. | 435/6 |
| 5,652,141 A | 7/1997 | Henco et al. | 435/270 |
| 5,856,174 A | 1/1999 | Lipshutz et al. | 435/286.5 |
| 5,882,903 A | 3/1999 | Andrevski et al. | 435/91.2 |
| 5,922,591 A | 7/1999 | Anderson et al. | 435/287.2 |
| 6,043,080 A | 3/2000 | Lipshutz et al. | 435/287.2 |
| 6,100,084 A | 8/2000 | Miles et al. | 435/306.1 |
| 6,168,948 B1 | 1/2001 | Anderson et al. | 435/287.2 |

FOREIGN PATENT DOCUMENTS

WO 99/33559 7/1999

* cited by examiner

Primary Examiner—Robert Raevis
(74) Attorney, Agent, or Firm—Townsend and Townsend and Crew LLP

(57) ABSTRACT

Embodiments of the invention facilitate processing of a fluid sample according to different protocols using the same apparatus, for instance, to determine the presence or absence of an analyte in the sample. In a specific embodiment, a fluid control and processing system for controlling fluid flow among a plurality of chambers comprises a body including a fluid sample processing region continuously coupled fluidicly with a fluid displacement chamber. The fluid displacement chamber is depressurizable to draw fluid into the fluid displacement chamber and pressurizable to expel fluid from the fluid displacement chamber. The body includes a plurality of external ports. The fluid sample processing region is fluidicly coupled with at least two of the external ports. The fluid displacement chamber is fluidicly coupled with at least one of the external ports. The body is adjustable with respect to the plurality of chambers to place at least one of the external ports selectively in fluidic communication with the plurality of chambers.

126 Claims, 30 Drawing Sheets

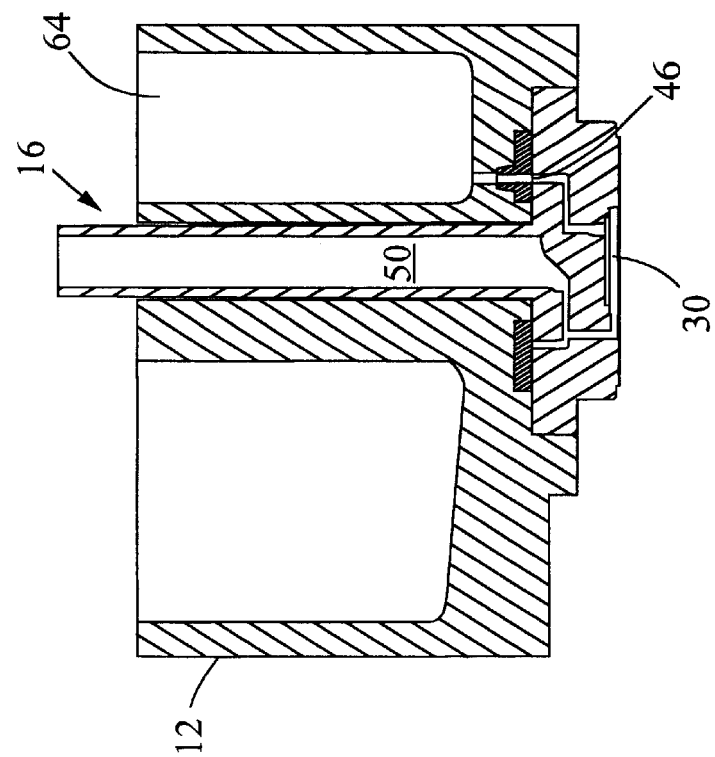
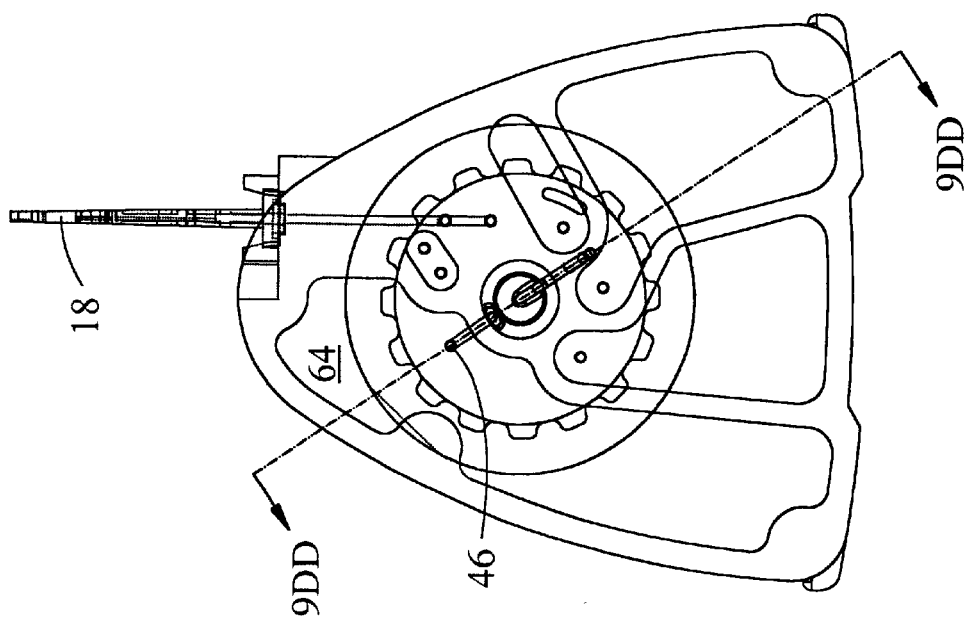
FIG. 9DD
FIG. 9D

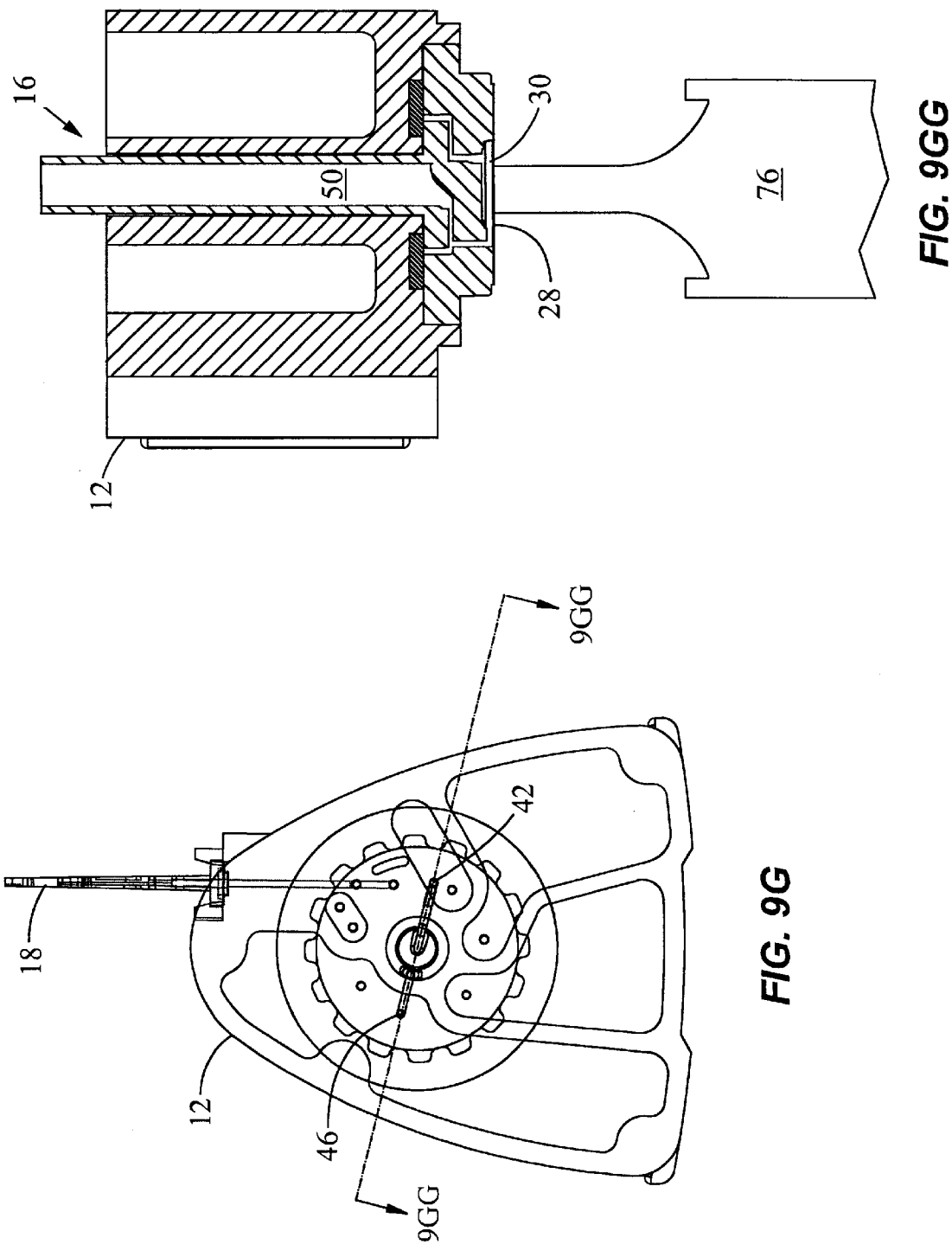

FIG. 9K'K'

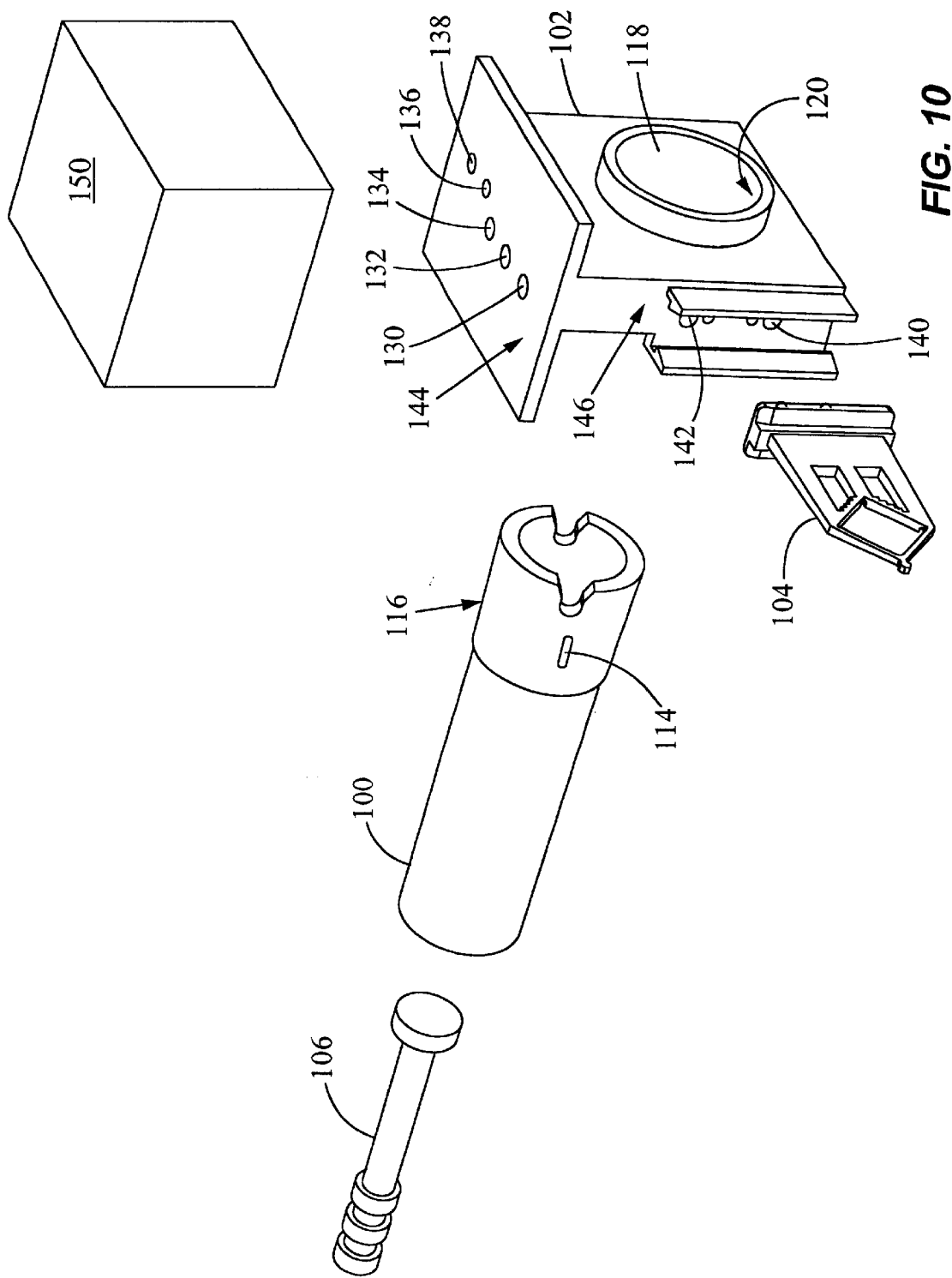

FLUID CONTROL AND PROCESSING SYSTEM

BACKGROUND OF THE INVENTION

The present invention relates generally to fluid manipulation and, more particularly, to a system and method for metering and distributing fluid for processing and analysis.

The analysis of fluids such as clinical or environmental fluids generally involves a series of processing steps, which may include chemical, optical, electrical, mechanical, thermal, or acoustical processing of the fluid samples. Whether incorporated into a bench-top instrument, a disposable cartridge, or a combination of the two, such processing typically involves complex fluidic assemblies and processing algorithms.

Conventional systems for processing fluid samples employ a series of chambers each configured for subjecting the fluid sample to a specific processing step. As the fluid sample flows through the system sequentially from chamber to chamber, the fluid sample undergoes the processing steps according to a specific protocol. Because different protocols require different configurations, conventional systems employing such sequential processing arrangements are not versatile or easily adaptable to different protocols.

SUMMARY OF THE INVENTION

The present invention provides an apparatus and method for manipulating fluids. Embodiments of the invention facilitate processing of a fluid sample according to different protocols using the same apparatus, for instance, to determine the presence or absence of an analyte in the sample. In a specific embodiment, the apparatus employs a rotary valve configuration that allows fluidic communication between a fluid sample processing region selectively with a plurality of chambers including, for example, a sample chamber, a waste chamber, a wash chamber, a lysate chamber, and a master-mix chamber. The fluid flow among the fluid sample processing region and the chambers is controlled by adjusting the position of the rotary valve. In this way, the metering and distribution of fluids in the apparatus can be varied depending on the specific protocol. Unlike conventional devices, the fluid flow is no longer limited to a specific protocol. As a result, the apparatus is more versatile and robust, and is adaptable to different protocols.

In accordance with an aspect of the present invention, a fluid control and processing system for controlling fluid flow among a plurality of chambers comprises a body including a fluid sample processing region continuously coupled fluidically with a fluid displacement chamber. The fluid displacement chamber is depressurizable to draw fluid into the fluid displacement chamber and pressurizable to expel fluid from the fluid displacement chamber. The body includes a plurality of external ports. The fluid sample processing region includes a plurality of fluid processing ports each fluidicly coupled with one of the external ports. The fluid displacement chamber is fluidicly coupled with at least one of the external ports. The body is adjustable with respect to the plurality of chambers to allow the external ports to be placed selectively in fluidic communication with the plurality of chambers.

In some embodiments, the body is adjustable with respect to the chambers to place one external port at a time in fluidic communication with one of the plurality of chambers. The fluid sample processing region is disposed between the fluid displacement chamber and at least one external port. The fluid sample processing region comprises an active member which includes, for example, a microfluidic chip, a solid phase material, a filter or a filter stack, an affinity matrix, a magnetic separation matrix, a size exclusion column, a capillary tube, or the like. An energy transmitting member is operatively coupled with the fluid sample processing region for transmitting energy thereto to process fluid contained therein. In one embodiment, the body includes a crossover channel, and the body is adjustable with respect to the plurality of chambers to place the crossover channel in fluidic communication between two of the chambers.

In accordance with another aspect of the invention, a fluid control and processing system for controlling fluid flow among a plurality of chambers comprises a body including a fluid sample processing region continuously coupled fluidically with a fluid displacement chamber. The fluid displacement chamber is depressurizable to draw fluid into the fluid displacement chamber and pressurizable to expel fluid from the fluid displacement chamber. The body includes a plurality of external ports. The fluid sample processing region is fluidicly coupled with at least two of the external ports. The fluid displacement chamber is fluidicly coupled with at least one of the external ports. The body is adjustable with respect to the plurality of chambers to place at least one of the external ports selectively in fluidic communication with the plurality of chambers.

In some embodiments, the body is adjustable with respect to the plurality of chambers to place at most one external port at a time in fluidic communication with one of the plurality of chambers. The body is also adjustable with respect to the plurality of chambers to close the external ports so that the fluid displacement chamber and sample fluid processing region are fluidicly isolated from the chambers. The fluid sample processing region comprises a trapping member for trapping sample components (e.g., cells, spores, viruses, large or small molecules, or proteins) of a fluid sample. The trapping member may comprise one or more filters, a microfluidic chip, filter paper, beads, fibers, a membrane, glass wool, polymers, or gel.

Another aspect of the invention is a method for controlling fluid flow between a valve and a plurality of chambers. The valve includes a plurality of external ports and a fluid displacement chamber continuously coupled fluidicly with a fluid sample processing region which is fluidicly coupled with at least two of the external ports. The method comprises adjusting the valve with respect to the plurality of chambers to place the external ports selectively in fluidic communication with the plurality of chambers.

BRIEF DESCRIPTION OF THE DRAWINGS

FIGS. 9A–9LL are top plan views and cross-sectional views illustrating a specific protocol for controlling and processing fluid using the fluid control and processing system of FIG. 1;

FIG. 10 is an exploded perspective view of the fluid control and processing system according to another embodiment of the present invention;

DESCRIPTION OF THE SPECIFIC EMBODIMENTS

Figure 1:
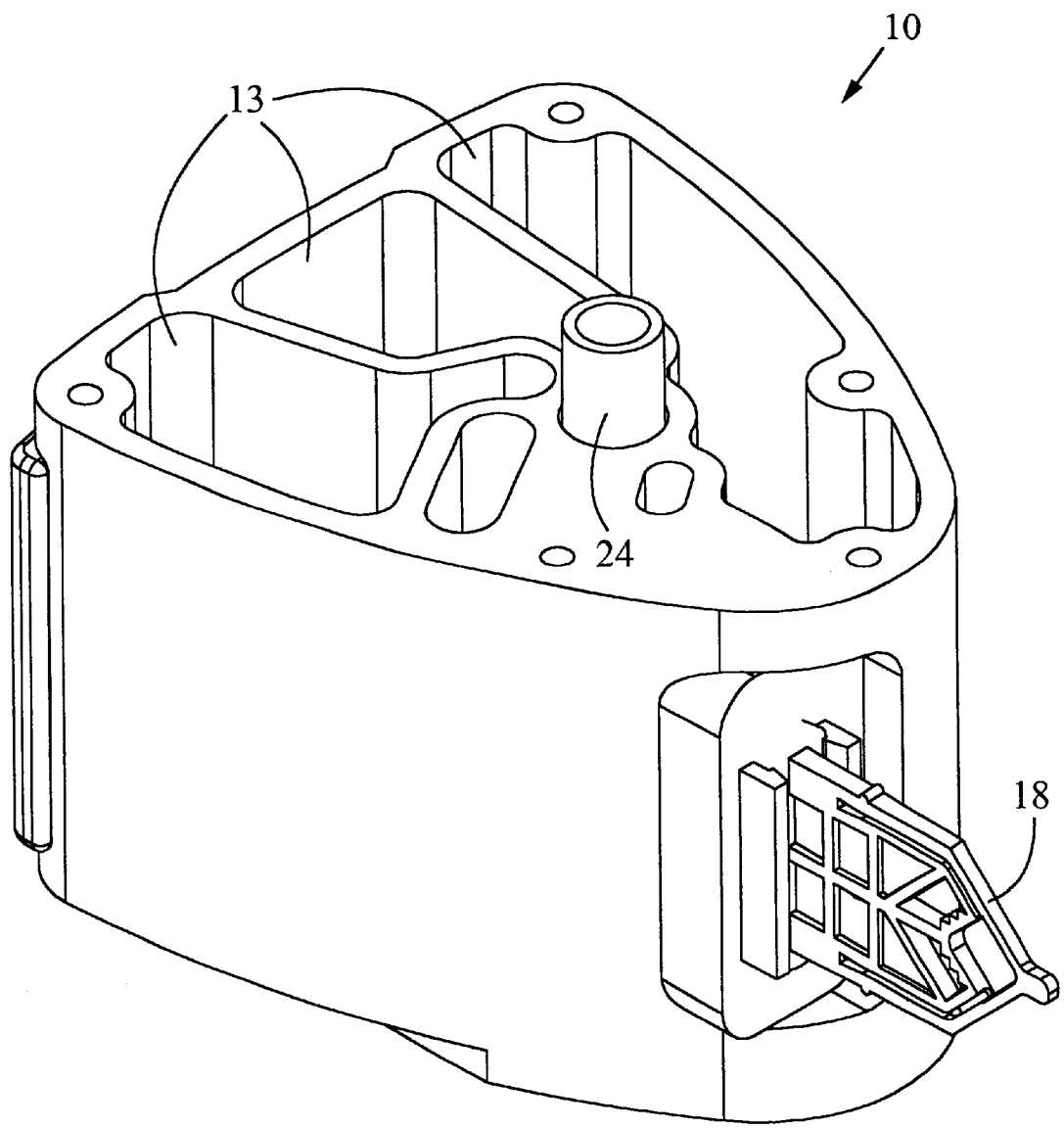
FIG. 1 is a perspective view of the fluid control and processing system according to an embodiment of the present invention.
Figure 2:
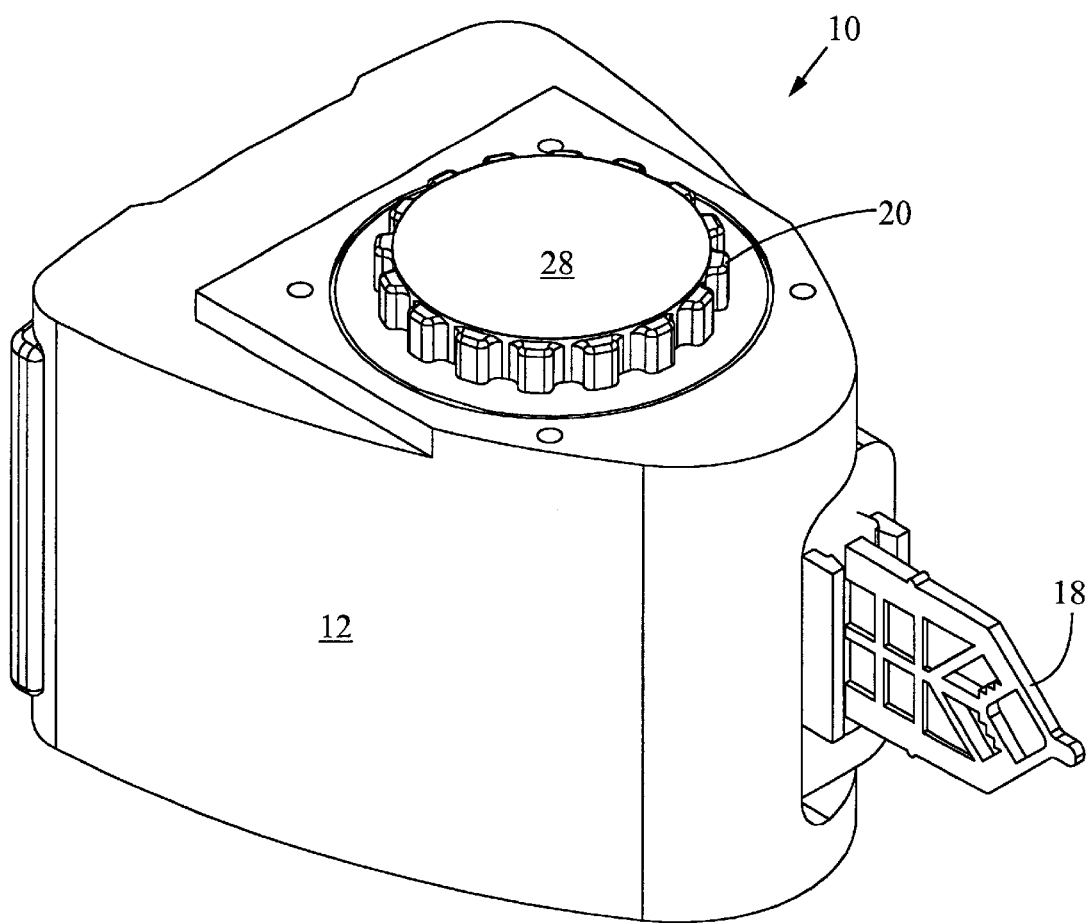
FIG. 2 is another perspective view of the system of FIG. 1.
Figure 3:
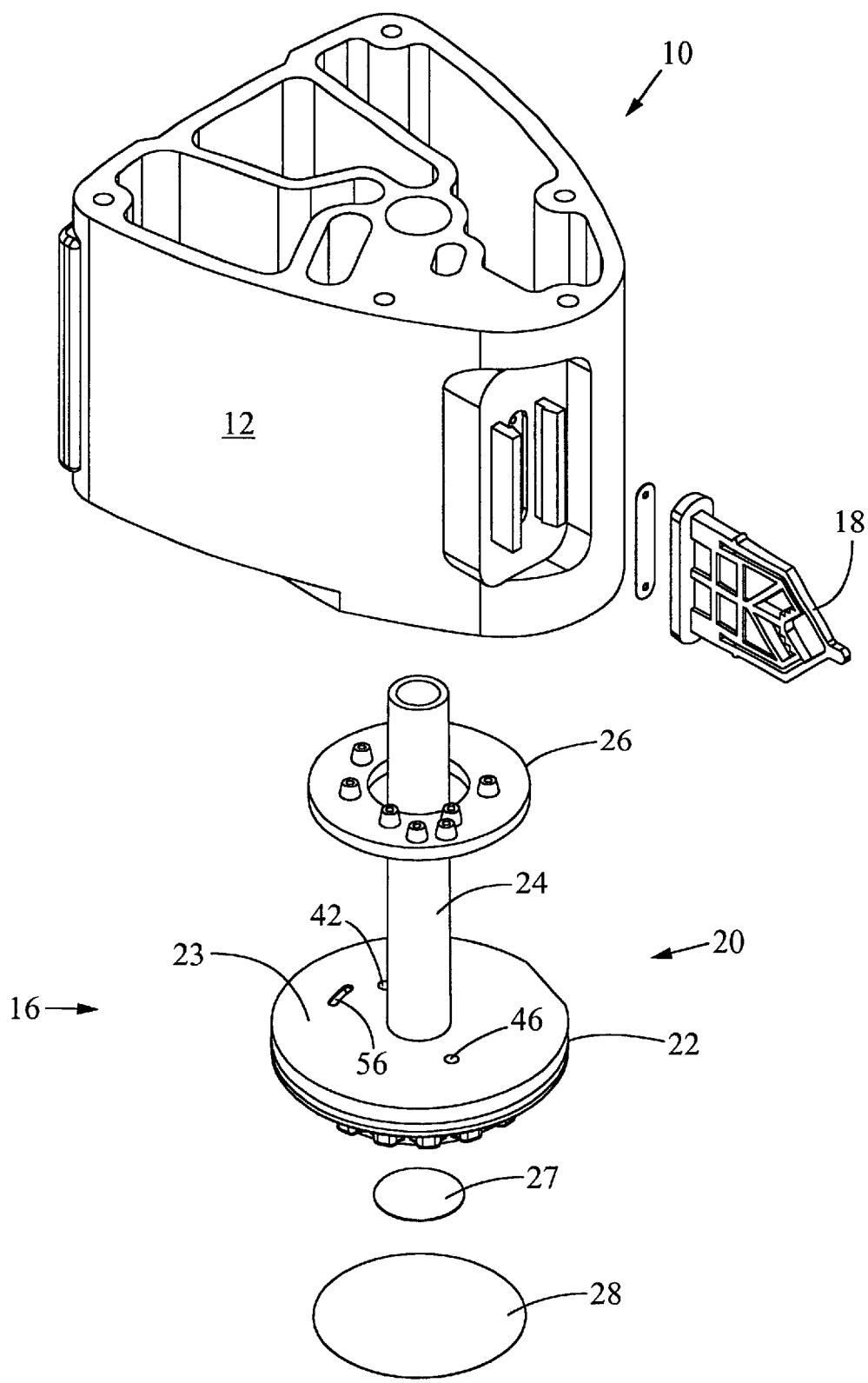
FIG. 3 is an exploded view of the system of FIG. 1.
Figure 4:
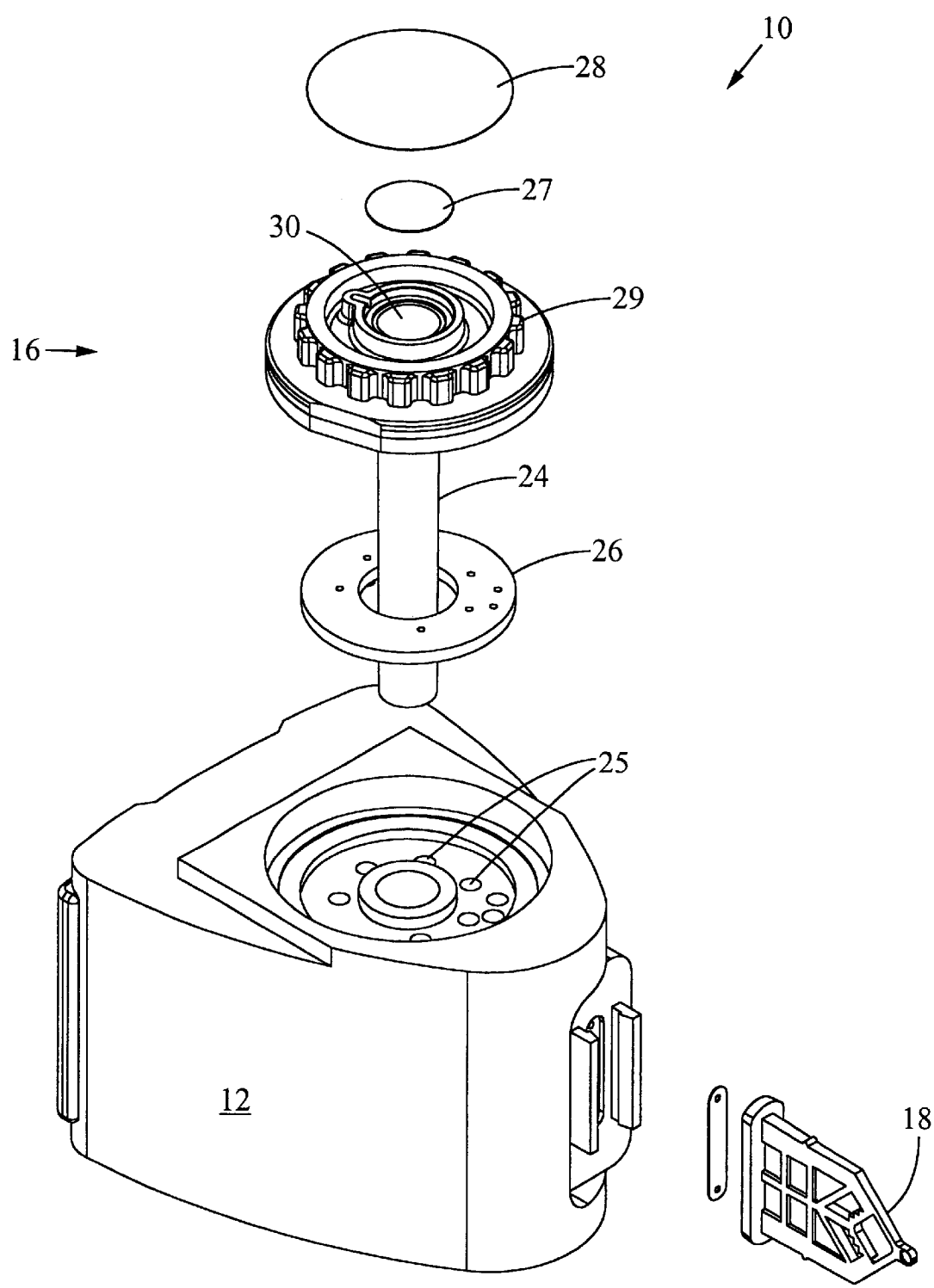
FIG. 4 is an exploded view of the system of FIG. 2.
Figure 5:
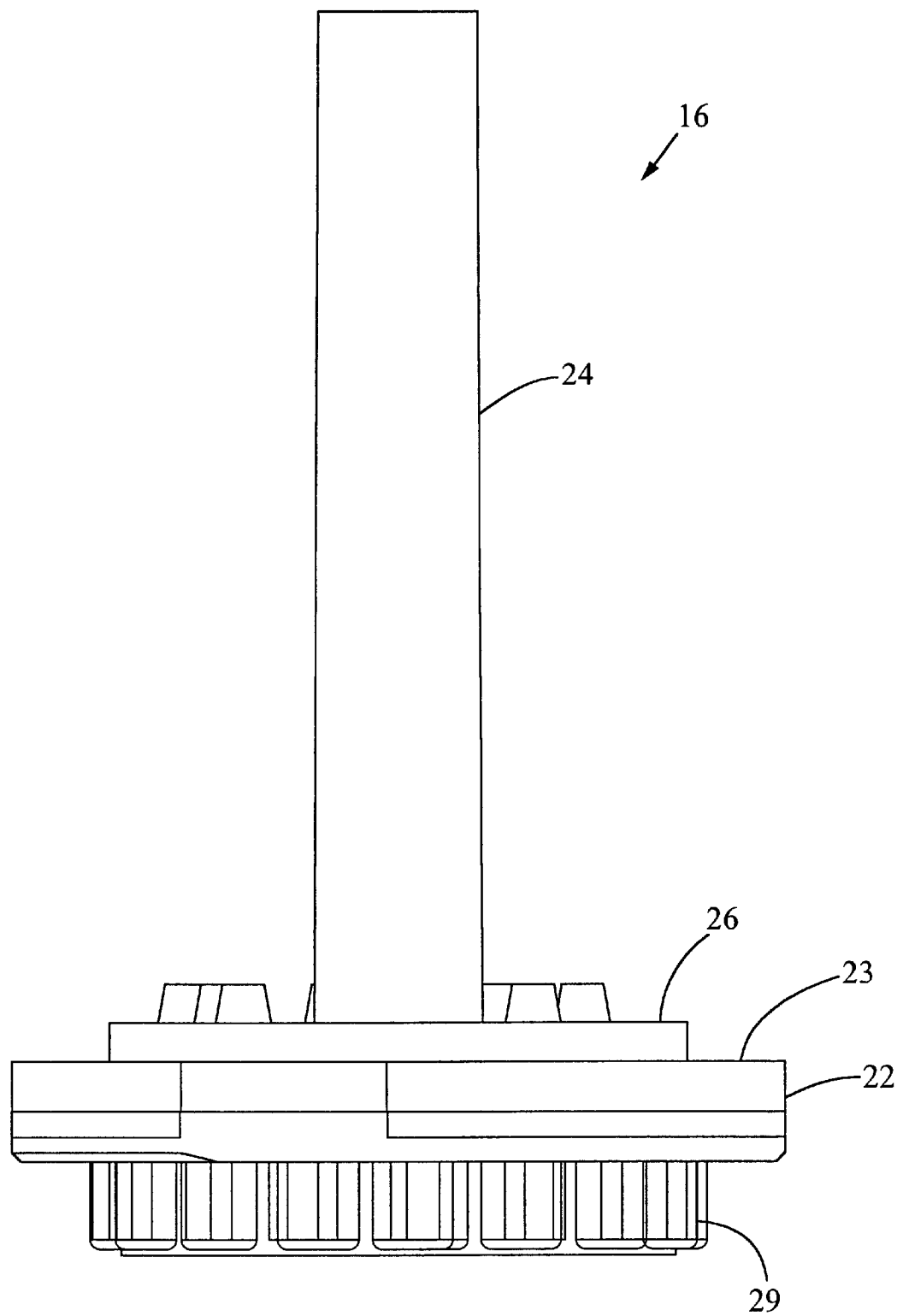
FIG. 5 is an elevational view of a fluid control apparatus and gasket in the system of FIG. 1.

FIGS. 1–4 show a fluid control and processing system 10 including a housing 12 having a plurality of chambers 13. FIG. 1 shows the chambers 13 exposed for illustrative purposes. A top cover will typically be provided to enclose the chambers 13. As best seen in FIGS. 3 and 4, a fluid control device 16 and a reaction vessel 18 are connected to different portions of the housing 12. The fluid control device in the embodiment shown is a rotary fluid control valve 16. The valve 16 includes a valve body 20 having a disk portion 22 and a tubular portion 24. The disk portion 22 has a generally planar external port surface 23, as best seen in FIG. 3. The valve 16 is rotatable relative to the housing 12. The housing 12 includes a plurality of chamber ports 25 facing the external port surface 23 of the disk portion 22 of the valve 16 (FIG. 4) to permit fluidic communication between the chambers 13 and the valve 16. A optional seal or gasket 26 is disposed between the disk portion 22 and the housing 12. The disk portion 22 further includes a filter or a filter stack 27 and an outer cover 28, and a toothed periphery 29. The cover 28 may be a rigid shell or a flexible film.

As best seen in FIG. 4, the disk portion 22 includes a fluid sample processing region 30. As used herein, the term "fluid sample processing region" refers to a region in which a fluid sample is subject to processing including, without limitation, chemical, optical, electrical, mechanical, thermal, or acoustical processing. For example, chemical processing may include a catalyst; optical processing may include U.V. activation; electrical processing may include electroporation or electrophoresis; mechanical processing may include filtering, pressurization, and cell disruption; thermal processing may include heating or cooling; and acoustical processing may include the use of ultrasound. The fluid sample processing region may include an active member, such as the filter 27, to facilitate processing of the fluid. Examples of active members include a microfluidic chip, a solid phase material, a filter or a filter stack, an affinity matrix, a magnetic separation matrix, a size exclusion column, a capillary tube, or the like. Suitable solid phase materials include, without limitation, beads, fibers, membranes, filter paper, glass wool, polymers, or gels. In a specific embodiment, the fluid sample processing region is used to prepare a sample for further processing, for instance, in the reaction vessel 18.

Figure 6:
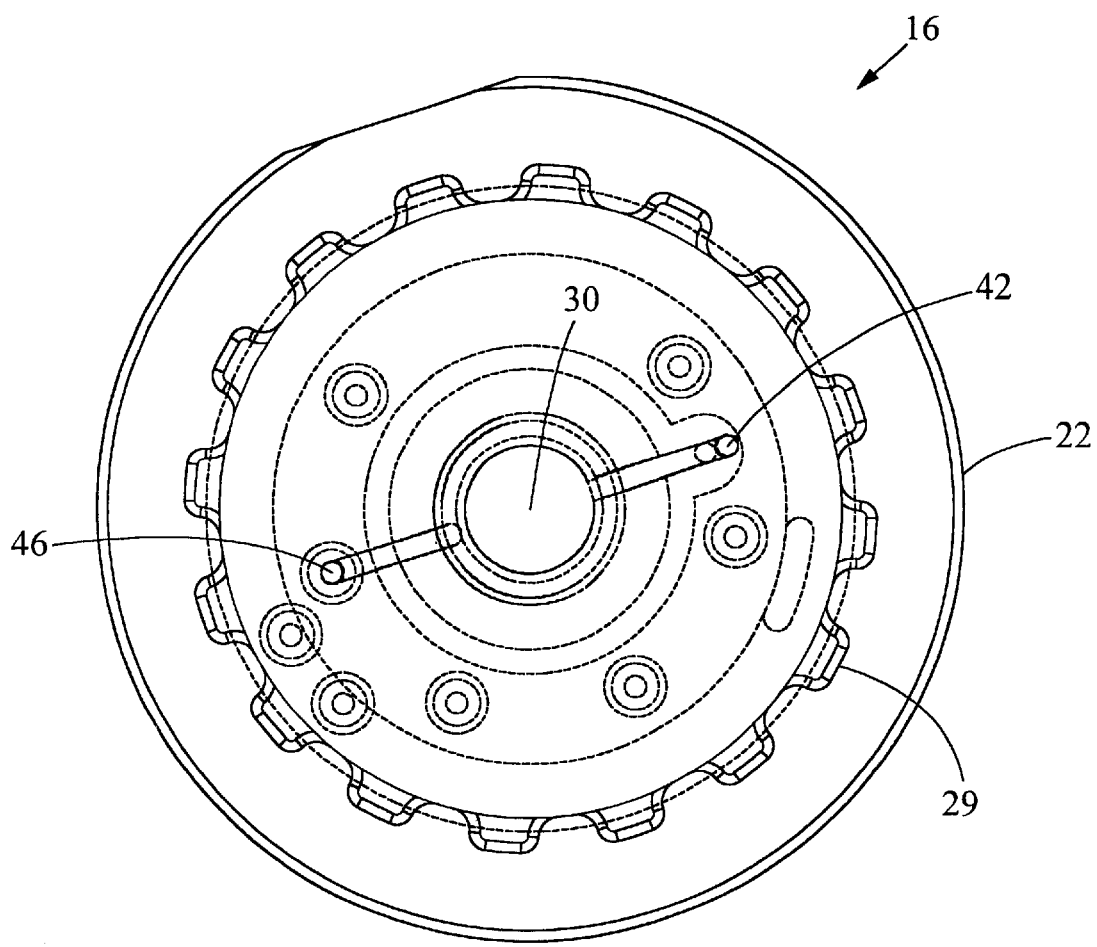
FIG. 6 is a bottom plan view of the fluid control apparatus and gasket of FIG. 5.
Figure 7:
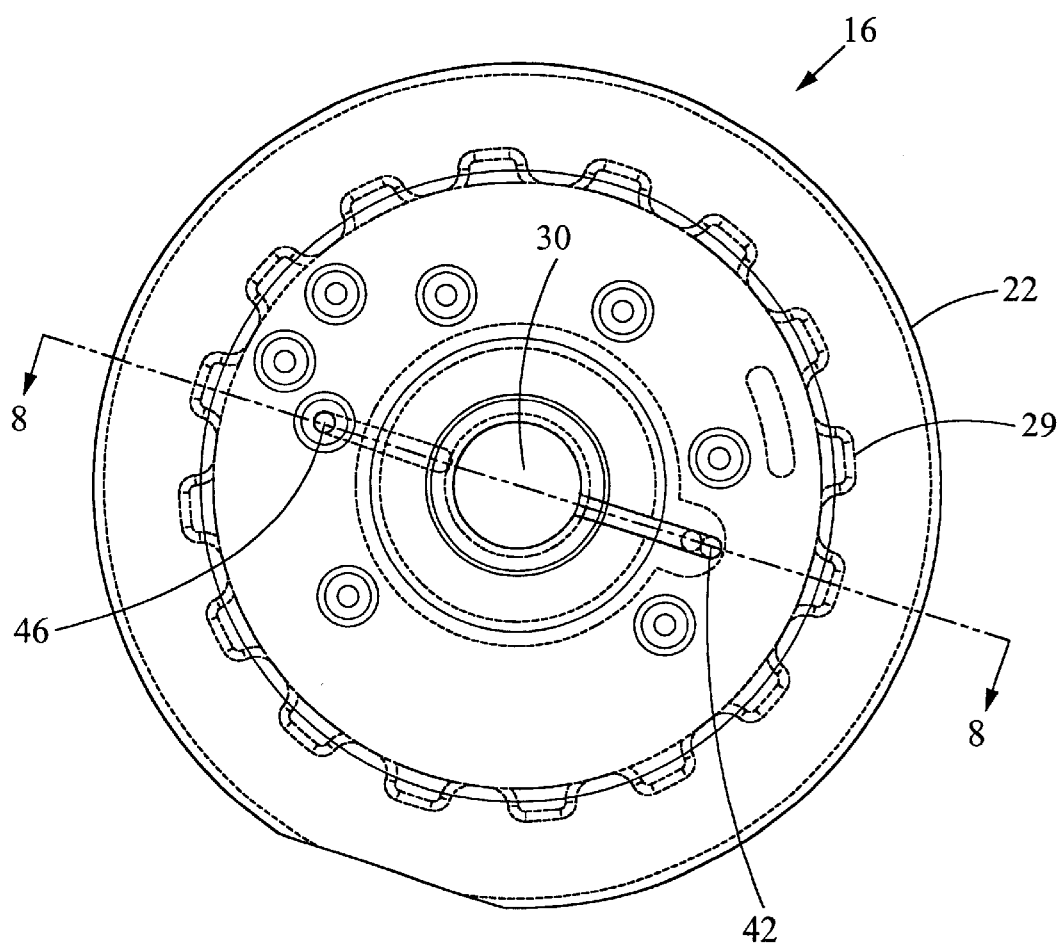
FIG. 7 is a top plan view of the fluid control apparatus and gasket of FIG. 5.
Figure 8:
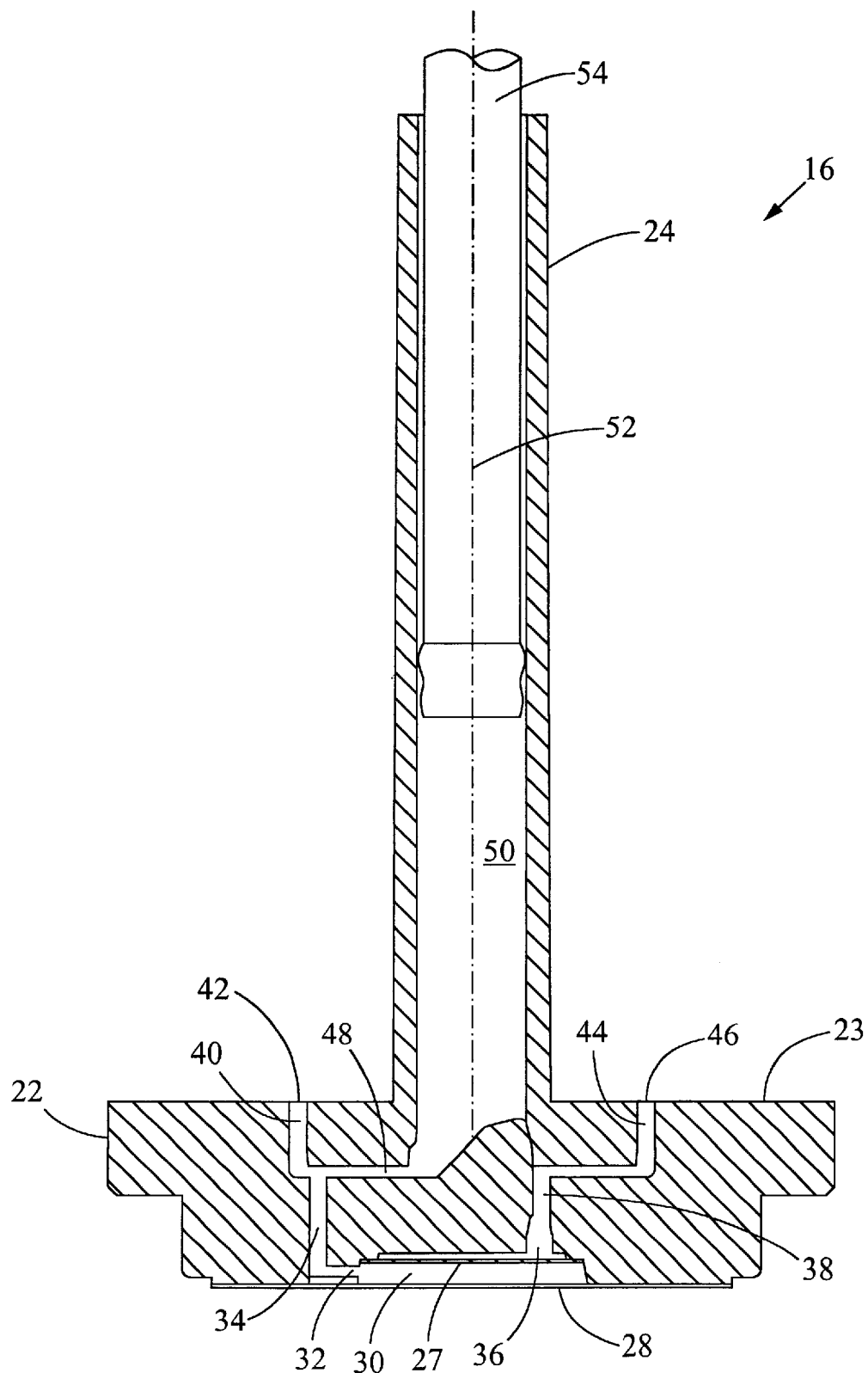
FIG. 8 is a cross-sectional view of the rotary fluid control apparatus of FIG. 7 along 8—8.

As shown in FIGS. 5–8, the outer cover 28 encloses the fluid sample processing region 30 and the bottom end of the disk portion 22 of the valve 16. In FIG. 8, the processing region 30 includes a first fluid processing port 32 coupled to a first fluid processing channel 34, and a second fluid processing port 36 coupled to a second fluid processing channel 38. The first fluid processing channel 34 is coupled to a first outer conduit 40 ending at a first external port 42 at the external port surface 23, while the second fluid processing channel 38 is coupled to a second outer conduit 44 ending at a second external port 46 at the external port surface 23. A fluid displacement channel 48 is coupled to the first fluid processing channel 34 and first conduit 40 near one end, and to a fluid displacement chamber 50 at the other end. The first outer conduit 40 serves as a common conduit for allowing fluidic communication between the first external port 42 and either or both of the first fluid processing channel 34 and the fluid displacement channel 48. The processing region 30 is in continuous fluidic communication with the fluid displacement chamber 50.

As shown in FIGS. 6–8, the external ports 42, 46 are angularly spaced from one another relative to the axis 52 of the valve 16 by about 180°. The external ports 42, 46 are spaced radially by the same distance from the axis 52. The axis 52 is perpendicular to the external port surface 23. In another embodiment, the angular spacing between the external ports 42, 46 may be different. The configuration of the channels in the disk portion 22 may also be different in another embodiment. For example, the first fluid processing channel 34 and the first outer conduit 40 may be slanted and coupled directly with the fluid displacement chamber 50, thereby eliminating the fluid displacement channel 48. The second fluid displacement channel 38 may also be slanted and extend between the second fluid processing port 36 and the second external port 46 via a straight line, thereby eliminating the second outer conduit 44. In addition, more channels and external ports may be provided in the valve 16. As best seen in FIG. 3, a crossover channel or groove 56 is desirably provided on the external port surface 23. The groove 56 is curved and desirably is spaced from the axis 52 by a constant radius. In one embodiment, the groove 56 is a circular arc lying on a common radius from the axis 52. As discussed in more detail below, the groove 56 is used for filling the vessel.

As shown in FIG. 8, the fluid displacement chamber 50 is disposed substantially within the tubular portion 24 of the valve 16 and extends partially into the disk portion 22. A fluid displacement member in the form of a plunger or piston 54 is movably disposed in the chamber 50. When the piston 54 moves upward, it expands the volume of the chamber 50 to produce a suction for drawing fluid into the chamber 50. When the piston 54 moves downward, it decreases the volume of the chamber 50 to drive fluid out of the chamber 50.

As the rotary valve 16 is rotated around its axis 52 relative to the housing 12 of FIGS. 1–4, one of the external ports 42, 46 may be open and fluidicly coupled with one of the chambers 13 or reaction vessel 18, or both external ports 42, 46 may be blocked or closed. In this embodiment, at most only one of the external ports 42, 46 is fluidicly coupled with one of the chambers or reaction vessel 18. Other embodiments may be configured to permit both external ports 42, 46 to be fluidicly coupled with separate chambers or the reaction vessel 18. Thus, the valve 16 is rotatable with respect to the housing 12 to allow the external ports 42, 46 to be placed selectively in fluidic communication with a plurality of chambers which include the chambers 13 and the reaction vessel 18. Depending on which external port 42, 46 is opened or closed and whether the piston 54 is moved upward or downward, the fluid flow in the valve 16 can change directions, the external ports 42, 46 can each switch from being an inlet port to an outlet port, and the fluid flow may pass through the processing region 30 or bypass the processing region 30. In a specific embodiment, the first external port 42 is the inlet port so that the inlet side of the processing region 30 is closer to the fluid displacement chamber 50 than the outlet side of the processing region 30.

Figure 9A:
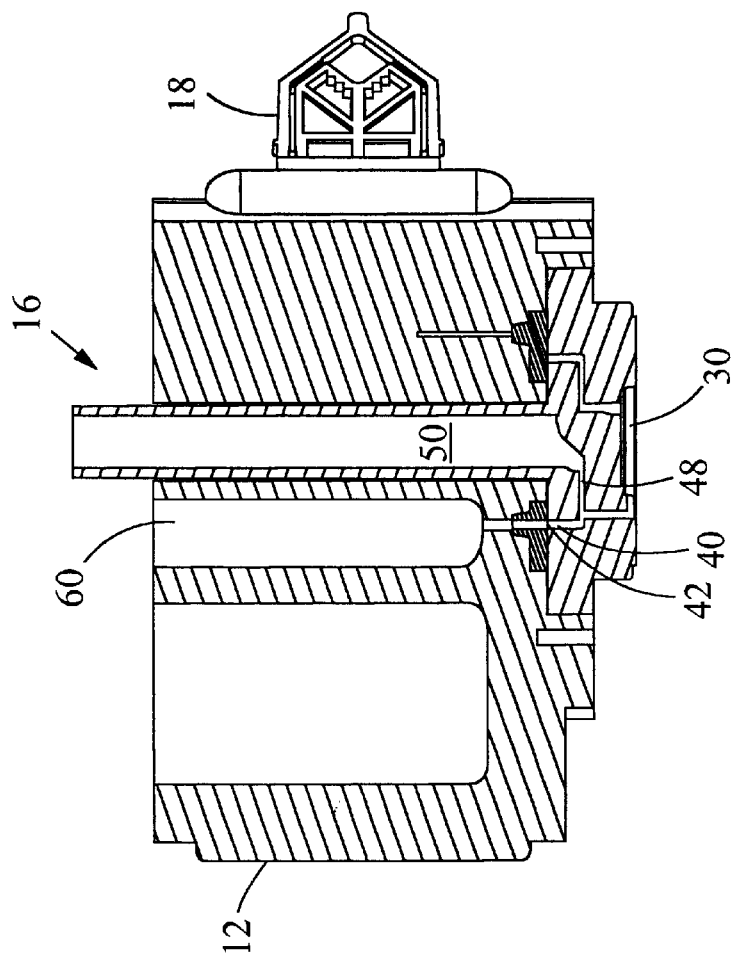
Figure 9A:
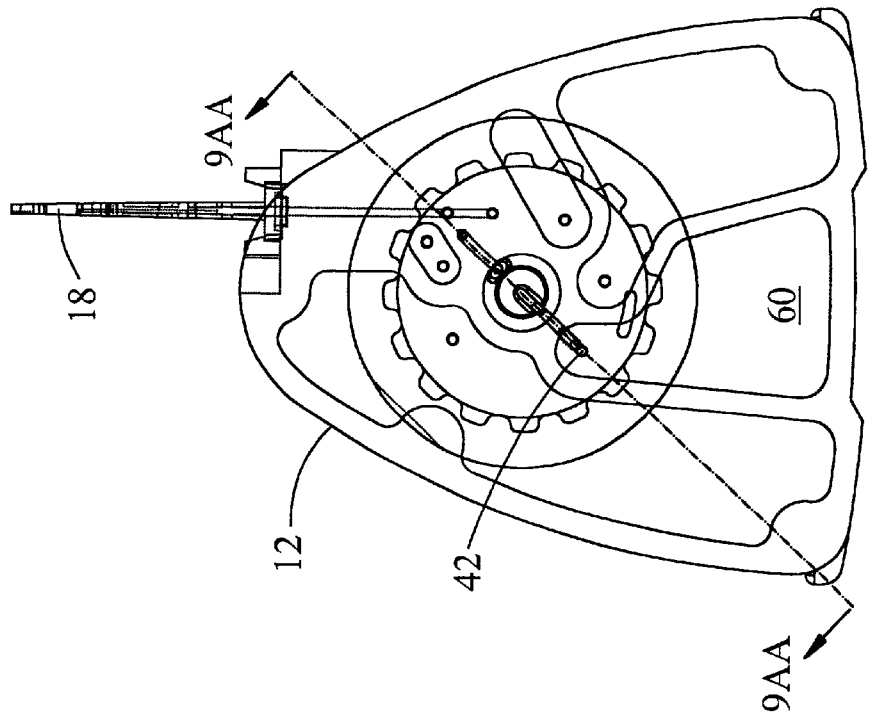
Figure 9B:
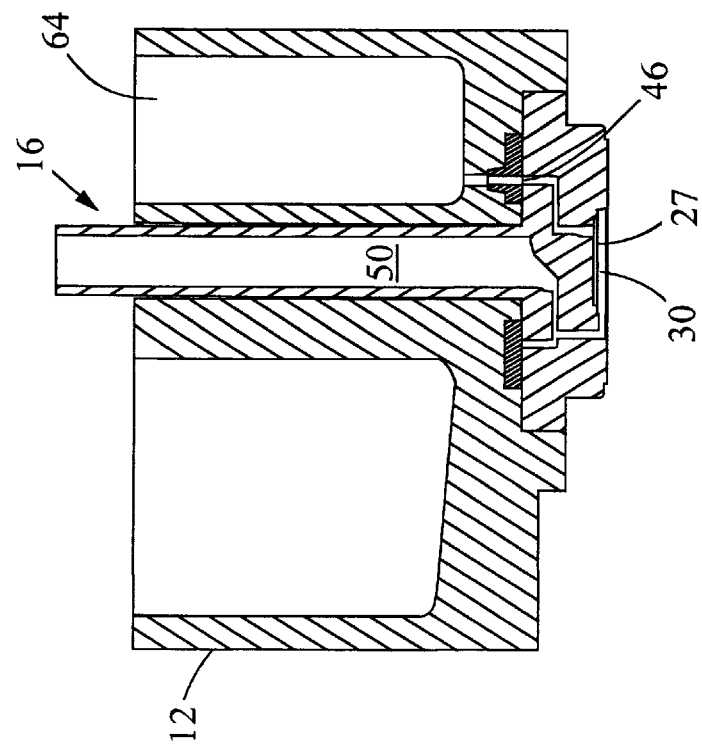
Figure 9B:
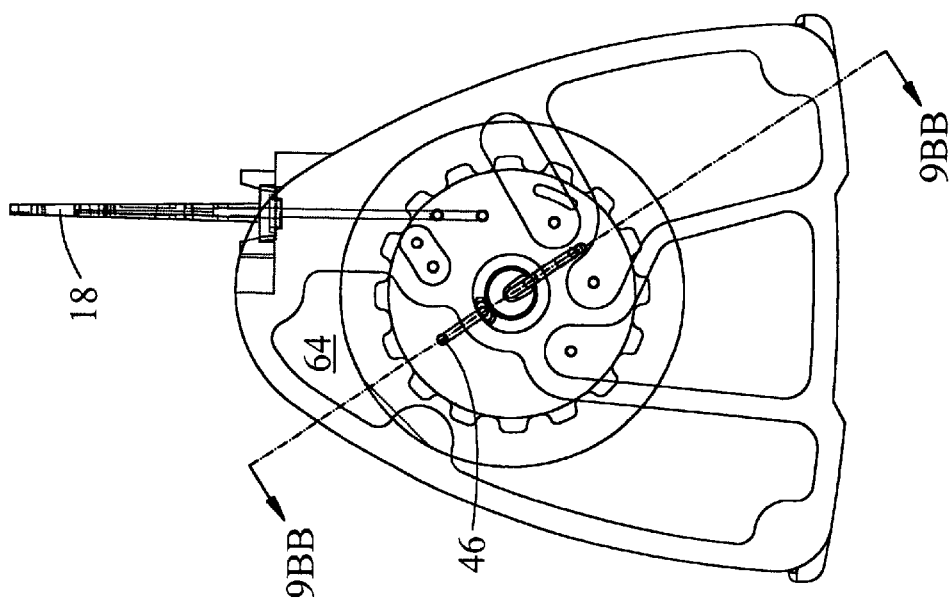

To demonstrate the fluid metering and distribution function of the valve 16, FIGS. 9A–9LL illustrate the operation of the valve 16 for a specific protocol. In FIGS. 9A and 9AA, the first external port 42 is placed in fluidic communication with a sample chamber 60 by rotating the valve 16, and the piston 54 is pulled upward to draw a fluid sample from the sample chamber 60 through the first outer conduit 40 and fluid displacement channel 48 to the fluid displacement chamber 50, bypassing the processing region 30. For simplicity, the piston 54 is not shown in FIGS. 9A–9LL. The valve 16 is then rotated to place the second external port 46 in fluidic communication with a waste chamber 64 as shown in FIGS. 9B and 9BB. The piston 54 is pushed downward to drive the fluid sample through the fluid sample processing region 30 to the waste chamber 64. In a specific embodiment, the fluid sample processing region 30 includes a filter or a filter stack 27 for capturing sample components (e.g., cells, spores, microorganisms, viruses, proteins, or the like) from the fluid sample as it passes therethrough. An example of a filter stack is described in commonly assigned, copending U.S. patent application Ser. No. 09/584,327, entitled "Apparatus and Method for Cell Disruption," filed May 30, 2000, which is incorporated herein by reference in its entirety. In alternative embodiments, other active members may be provided in the processing region 30. These first two steps of capturing sample components may be repeated as desired.

Figure 9C:
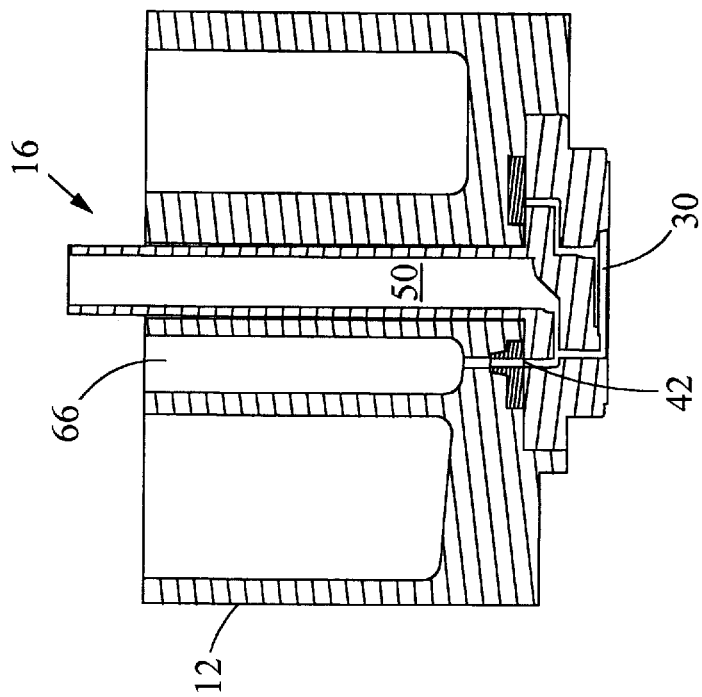
Figure 9C:
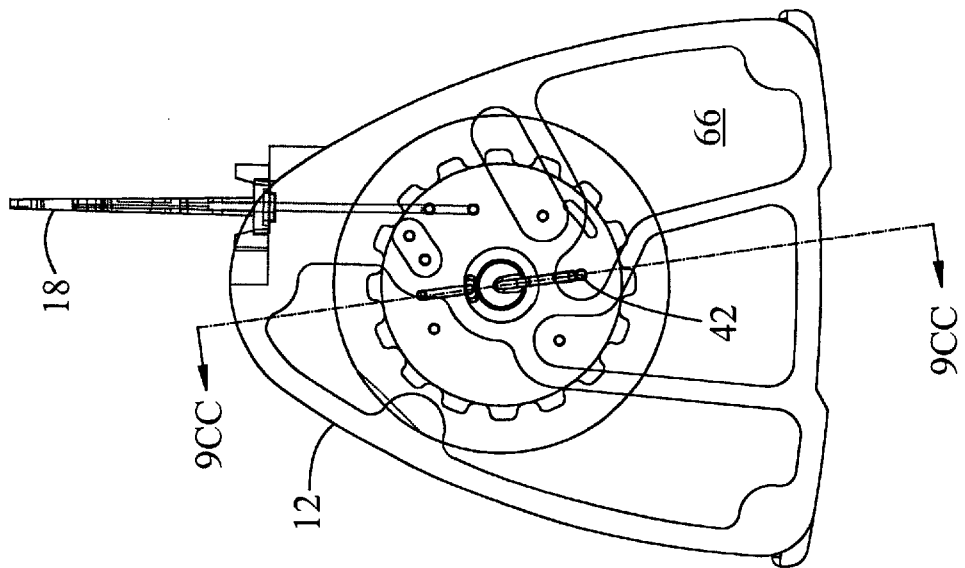

In FIGS. 9C and 9CC, the valve 16 is rotated to place the first external port 42 in fluidic communication with a wash chamber 66, and the piston 54 is pulled upward to draw a wash fluid from the wash chamber 66 into the fluid displacement chamber 50, bypassing the processing region 30. The valve 16 is then rotated to place the second external port 46 in fluidic communication with the waste chamber 64 as shown in FIGS. 9D and 9DD. The piston 54 is pushed downward to drive the wash fluid through the fluid sample processing region 30 to the waste chamber 64. The above washing steps may be repeated as desired. The intermediate washing is used to remove unwanted residue within the valve 16.

Figure 9E:
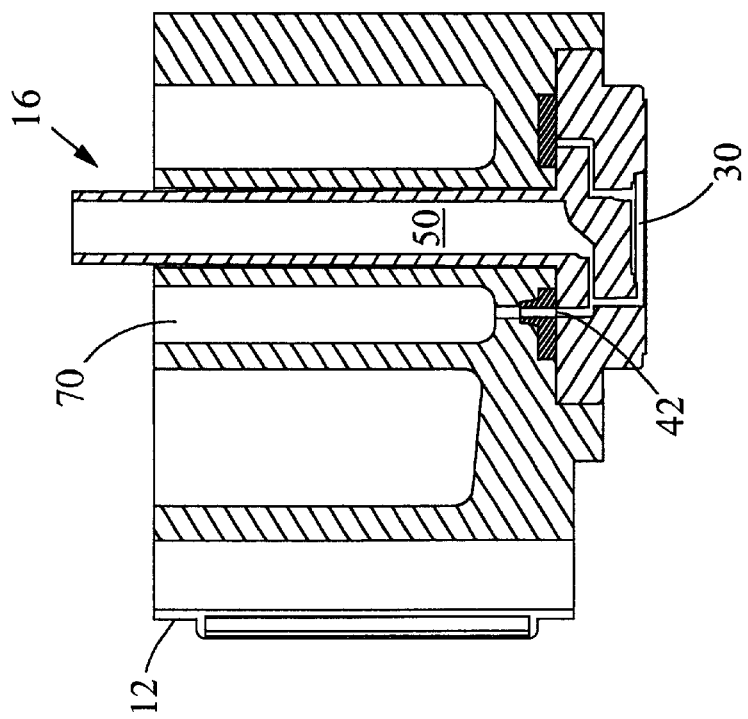
Figure 9E:
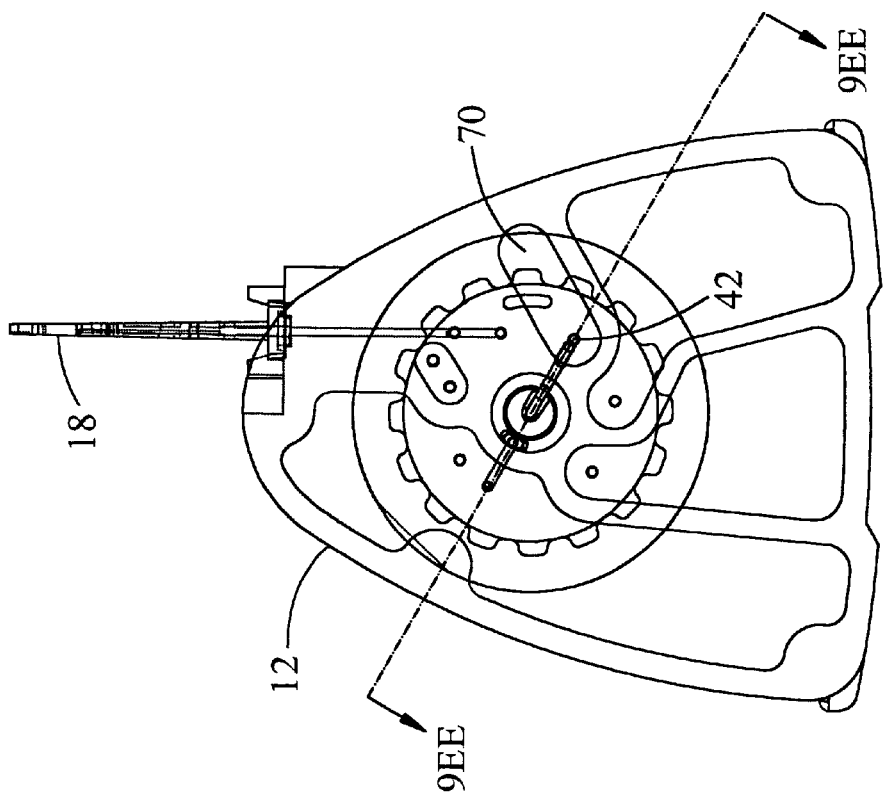
Figure 9F:
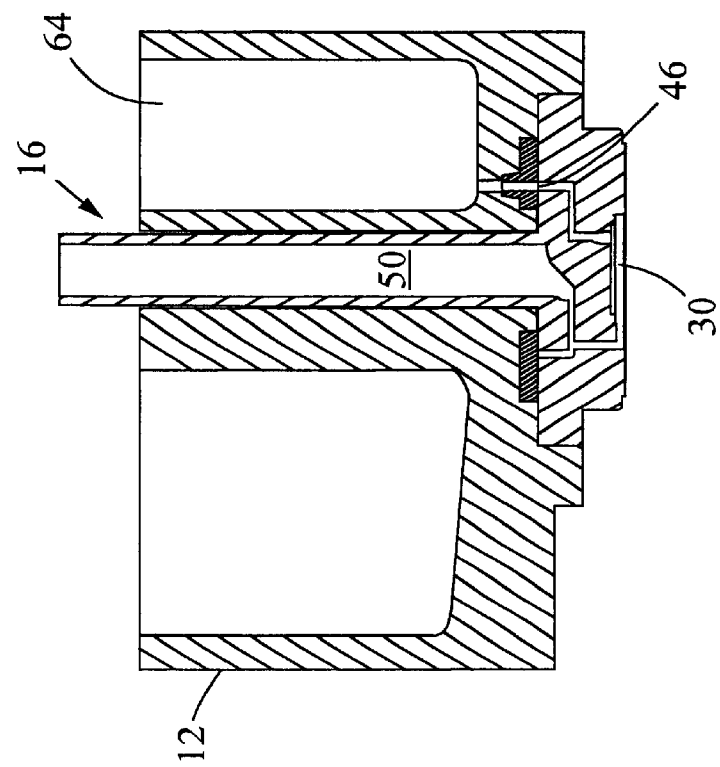
Figure 9F:
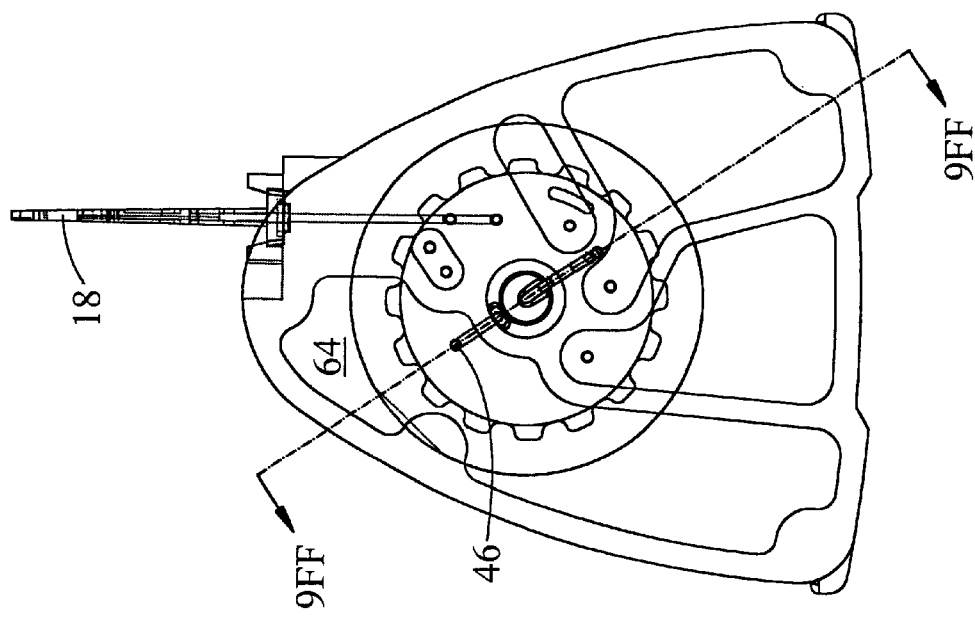

In FIGS. 9E and 9EE, the valve 16 is rotated to place the first external port 42 in fluidic communication with a lysate chamber 70, and the piston 54 is pulled upward to draw a lysate fluid (e.g., a lysing reagent or buffer) from the lysate chamber 70 into the fluid displacement chamber 50, bypassing the processing region 30. The valve 16 is then rotated to place the second external port 46 in fluidic communication with the waste chamber 64 as shown in FIGS. 9F and 9FF. The piston 54 is pushed downward to drive the lysate fluid through the fluid sample processing region 30 to the waste chamber 64. In FIGS. 9G, and 9GG, the valve 16 is rotated to close the external ports 42, 46. The piston 54 is pushed downward to pressurize the remaining lysate fluid and the sample components captured in the fluid sample processing region 30. Additional energy may be applied to the mixture in the processing region 30. For instance, a sonic member 76 such as an ultrasonic horn may be placed in contact with the outer cover 28 to transmit sonic energy into the processing region 30 to facilitate lysing of the sample components. In one embodiment, the outer cover 28 is made of a flexible film which is stretched under pressure to contact the sonic member 76 during lysing to allow transmission of the sonic energy into the processing region 30.

The cover 28 in one preferred embodiment is a flexible film of polymeric material such as polypropylene, polyethylene, polyester, or other polymers. The film may either be layered, e.g., laminates, or the films may be homogeneous. Layered films are preferred because they generally have better strength and structural integrity than homogeneous films. In particular, layered polypropylene films are presently preferred because polypropylene is not inhibitory to polymerase chain reaction (PCR). Alternatively, the cover 28 may comprise other materials such as a rigid piece of plastic.

In general, the energy transmitting member that is operatively coupled to the processing region 30 for transmitting energy thereto may be an ultrasonic, piezoelectric, magnetostrictive, or electrostatic transducer. The energy transmitting member may also be an electromagnetic device having a wound coil, such as a voice coil motor or a solenoid device. It is presently preferred that the energy transmitting member be a sonic member, such as an ultrasonic horn. Suitable horns are commercially available from Sonics & Materials, Inc. having an office at 53 Church Hill, Newton, Conn. 06470-1614, U.S.A. Alternatively, the sonic member may comprise a piezoelectric disk or any other type of ultrasonic transducer that may be coupled to the cover 28. In alternative embodiments, the energy transmitting member may be a thermal element (e.g., a heater) for transmitting thermal energy to the processing region 30 or an electrical element for transmitting electrical energy to the processing region 30. In addition, multiple energy transmitting members may be employed simultaneously, e.g., simultaneously heating and sonicating the processing region to effect lysis of cells, spores, viruses, or microorganisms trapped in the processing region.

Figure 9H:
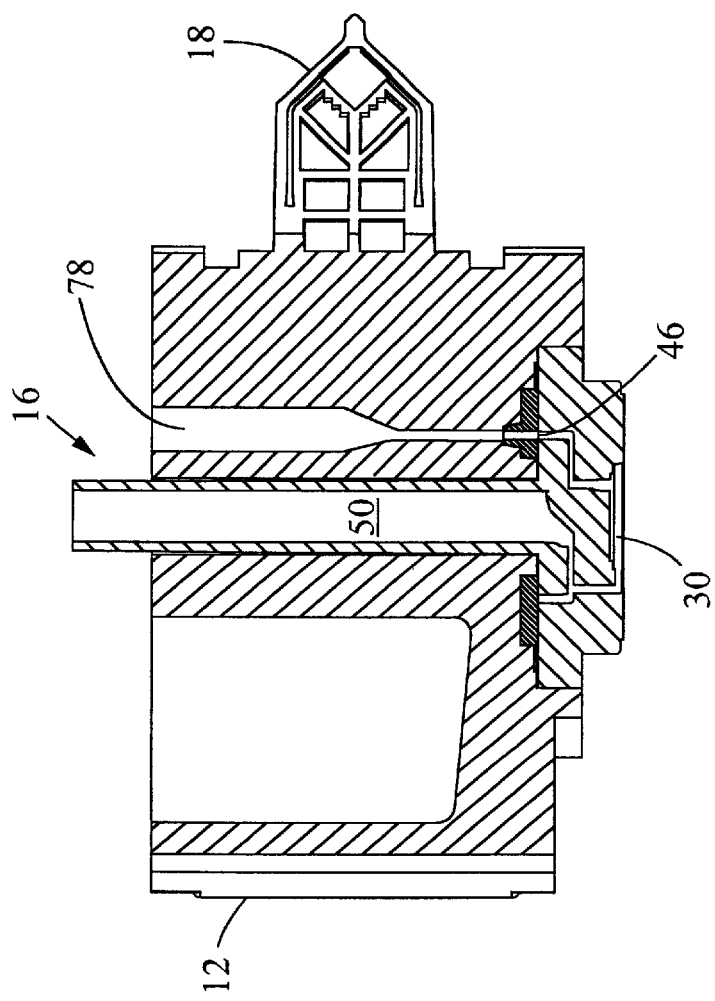
Figure 9H:
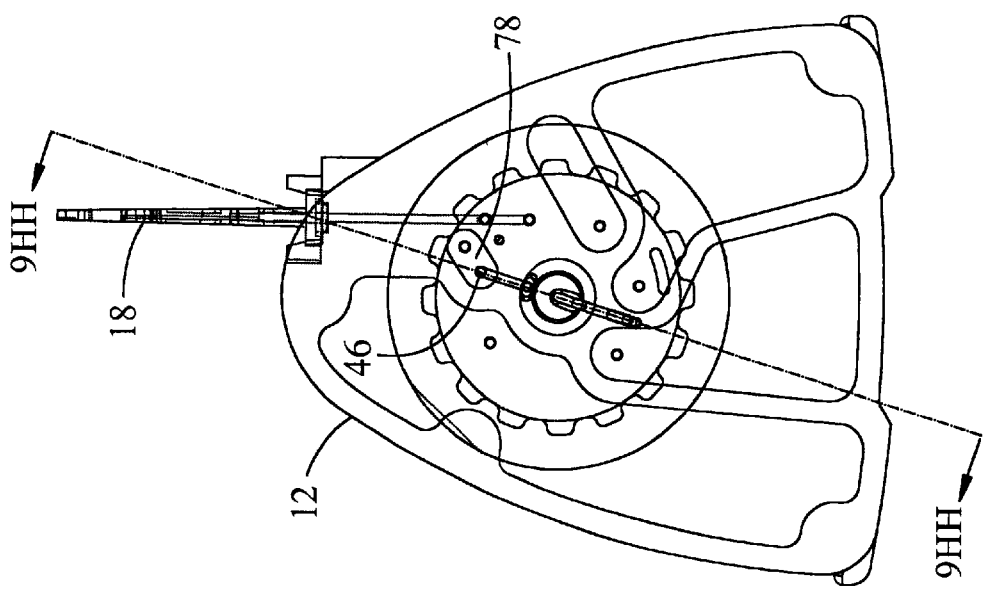
Figure 9I:
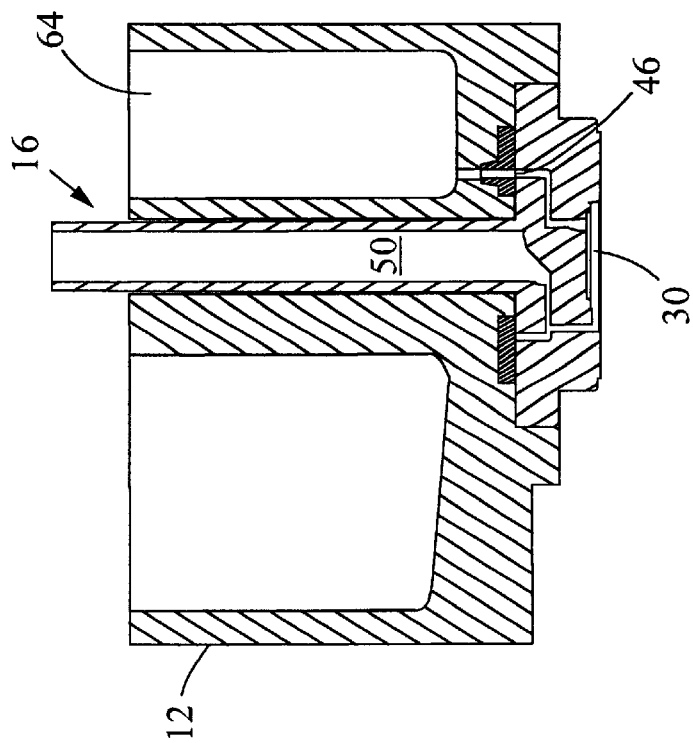
Figure 9I:
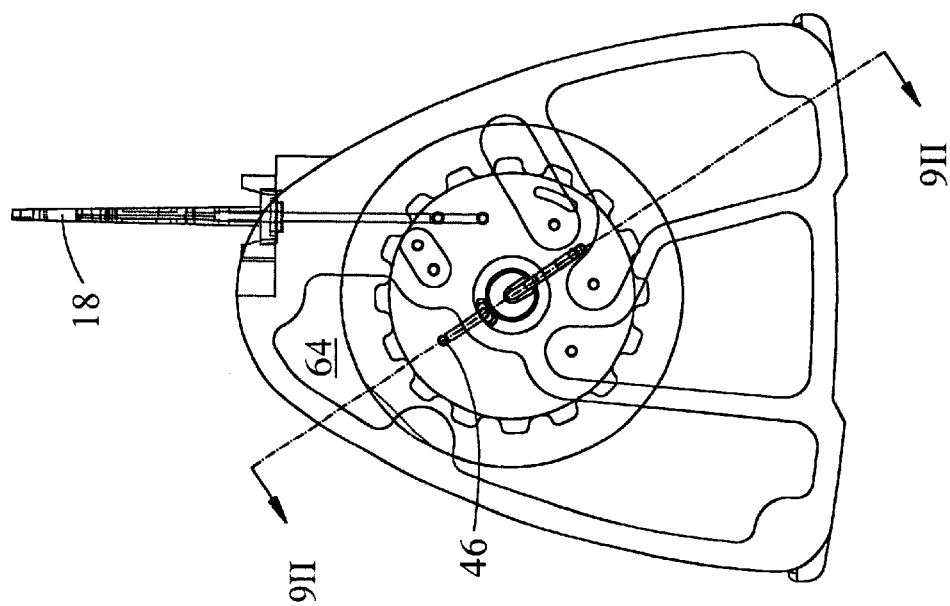
Figure 9J:
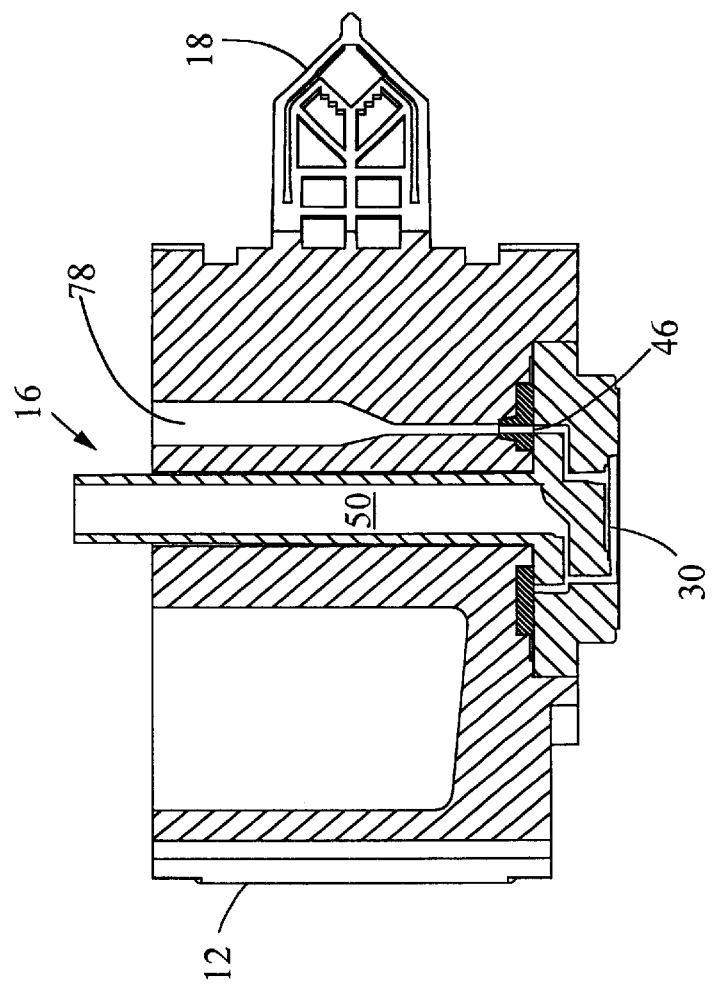
Figure 9J:
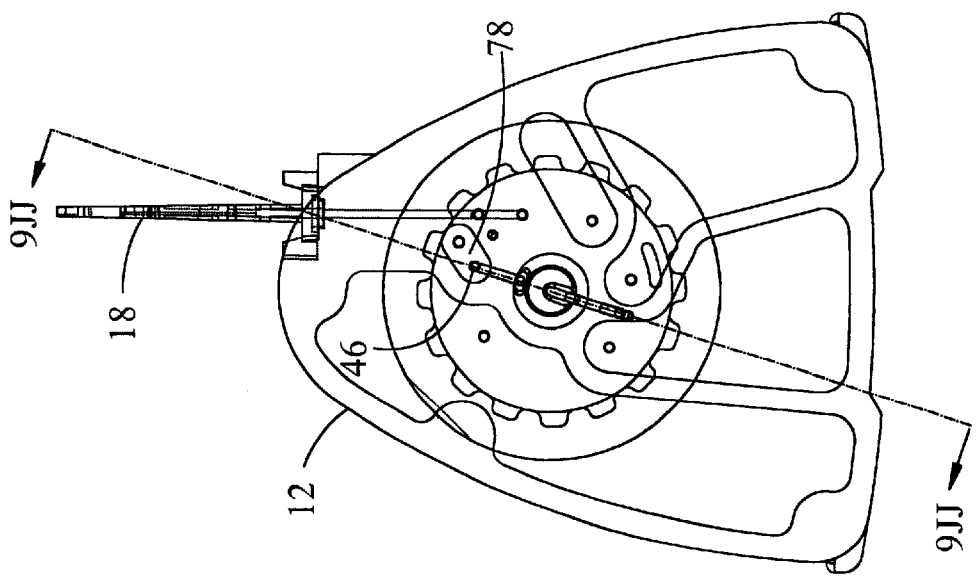

In FIGS. 9H and 9HH, the valve 16 is rotated to place the second external port 46 in fluidic communication with a mastermix chamber 78, and the piston 54 is pushed downward to elute the mixture from the processing region 30 to the mastermix chamber 78. The mastermix chamber 78 typically contains reagents (e.g., PCR reagents and fluorescent probes) to be mixed with the sample. Any excess mixture is dispensed into the waste chamber 64 via the second external port 46 after rotating the valve 16 to place the port 46 in fluidic communication with the waste chamber 64, as shown in FIGS. 9I and 9II. The mixture is then mixed in the mastermix chamber 78 by toggling. This is carried out by placing the fluid displacement chamber 50 in fluidic communication with the mastermix chamber 78 as shown in FIGS. 9J and 9JJ, and moving the piston 54 up and down. Toggling of the mixture through the filter in the processing region 30, for instance, allows larger particles trapped in the filter to temporarily move out of the way to permit smaller particles to pass through.

Figure 9K:
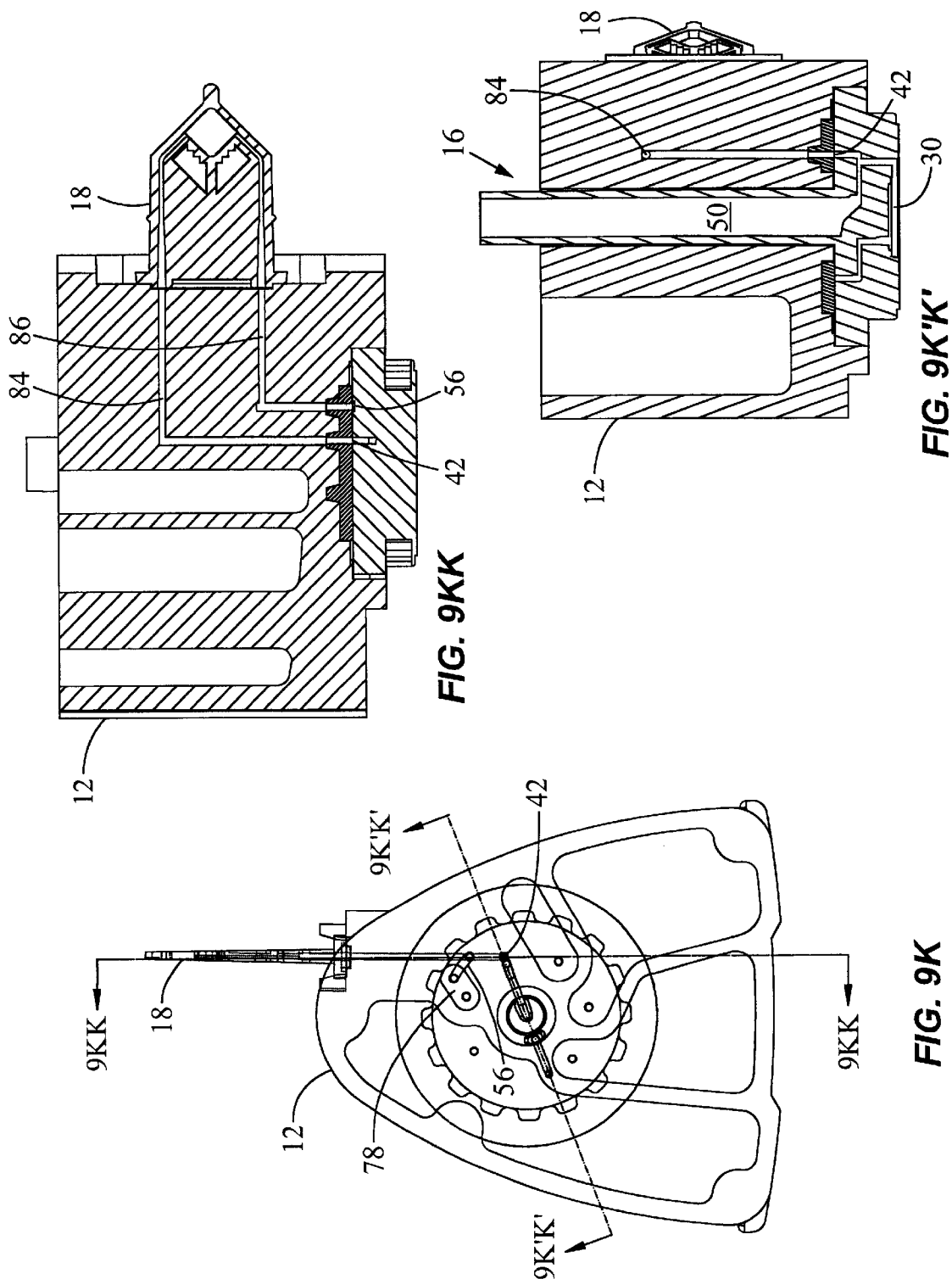

In FIGS. 9K, 9KK, and 9K'K', the valve 16 is rotated to place the first external port 42 in fluidic communication with a first branch 84 coupled to the reaction vessel 18, while the second branch 86 which is coupled to the reaction vessel 18 is placed in fluidic communication with the crossover groove 56. The first branch 84 and second branch 86 are disposed at different radii from the axis 52 of the valve 16, with the first branch 84 having a common radius with the first external port 42 and the second branch 86 having a common radius with the crossover groove 56. The crossover groove 56 is also in fluidic communication with the mastermix chamber 78 (FIG. 9K), and serves to bridge the gap between the mastermix chamber 78 and the second branch 86 to provide crossover flow therebetween. The external ports are disposed within a range of external port radii from the axis and the crossover groove is disposed within a range of crossover groove radii from the axis, where the range of external port radii and the range of crossover groove radii are non-overlapping. Placing the crossover groove 56 at a different radius from the radius of the external ports 42, 46 is advantageous because it avoids cross-contamination of the crossover groove 56 by contaminants that may be present in the area near the surfaces between the valve 16 and the housing 12 at the radius of the external ports 42, 46 as a result of rotational movement of the valve 16. Thus, while other configurations of the crossover groove may be used including those that overlap with the radius of the external ports 42, 46, the embodiment as shown is a preferred arrangement that isolates the crossover groove 56 from contamination from the area near the surfaces between the valve 16 and the housing 12 at the radius of the external ports 42, 46.

Figure 9L:
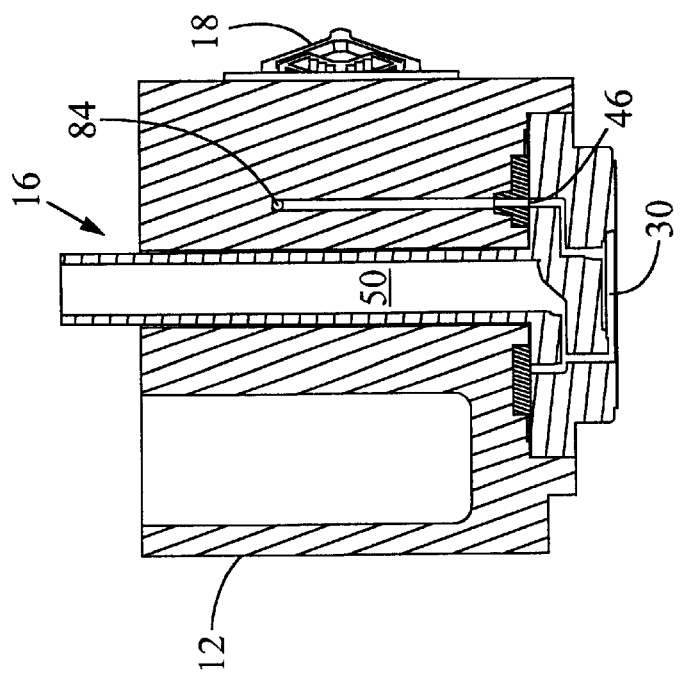
Figure 9L:
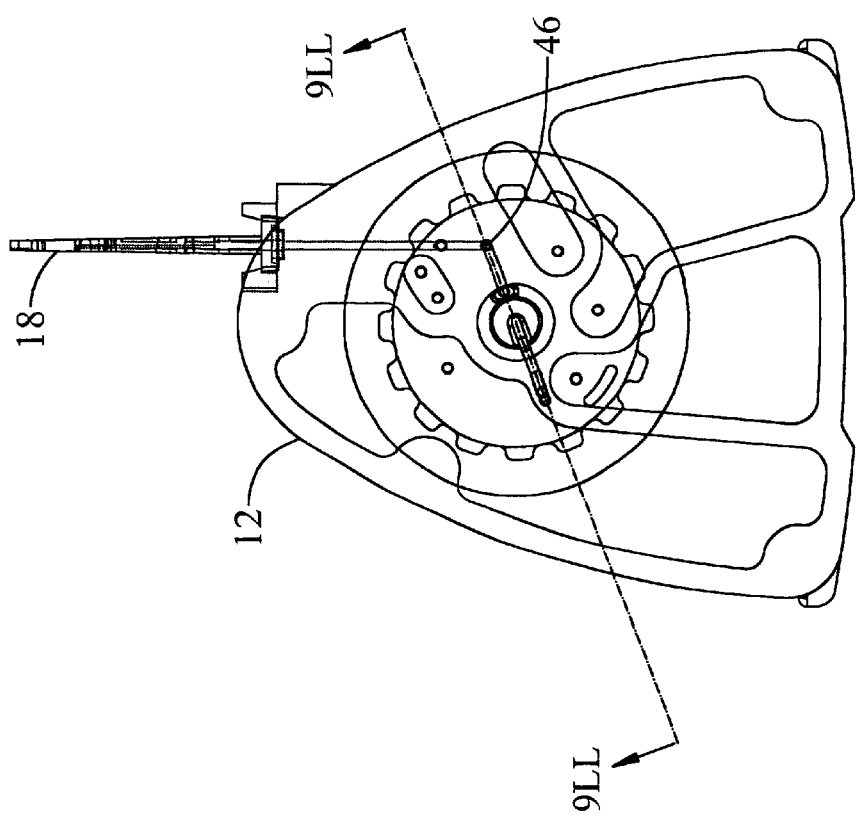

To fill the reaction vessel 18, the piston 54 is pulled upward to draw the mixture in the mastermix chamber 78 through the crossover groove 56 and the second branch 86 into the reaction vessel 18. In such an arrangement, the reaction vessel 18 is the aspiration chamber or referred to as the first chamber, and the mastermix chamber 78 is the source chamber or referred to as the second chamber. The valve 16 is then rotated to place the second external port 46 in fluidic communication with the first branch 84 and to close the first external port 42, as shown in FIGS. 9L and 9LL. The piston 54 is pushed downward to pressurize the mixture inside the reaction vessel 18. The reaction vessel 18 may be inserted into a thermal reaction chamber for performing nucleic acid amplification and/or detection. The two branches 84, 86 allow filling and evacuation of the reaction chamber of the reaction vessel 18. The vessel maybe connected to the housing 12 by ultrasonic welding, mechanical coupling, or the like, or be integrally formed with the housing 12 such as by molding. The use of a reaction vessel for analyzing a fluid sample is described in commonly assigned, copending U.S. patent application Ser. No. 09/584, 328, entitled "Cartridge for Conducting a Chemical Reaction," filed May 30, 2000.

To operate the valve 16 of FIGS. 3–8, a motor such as a stepper motor is typically coupled to the toothed periphery 29 of the disk portion 22 to rotate the valve 16 relative to the housing 12 for distributing fluid with high precision. The motor can be computer-controlled according to the desired protocol. A linear motor or the like is typically used to drive the piston 54 up and down with precision to provide accurate metering, and may also be computer-controlled according to the desired protocol.

Figure 11:
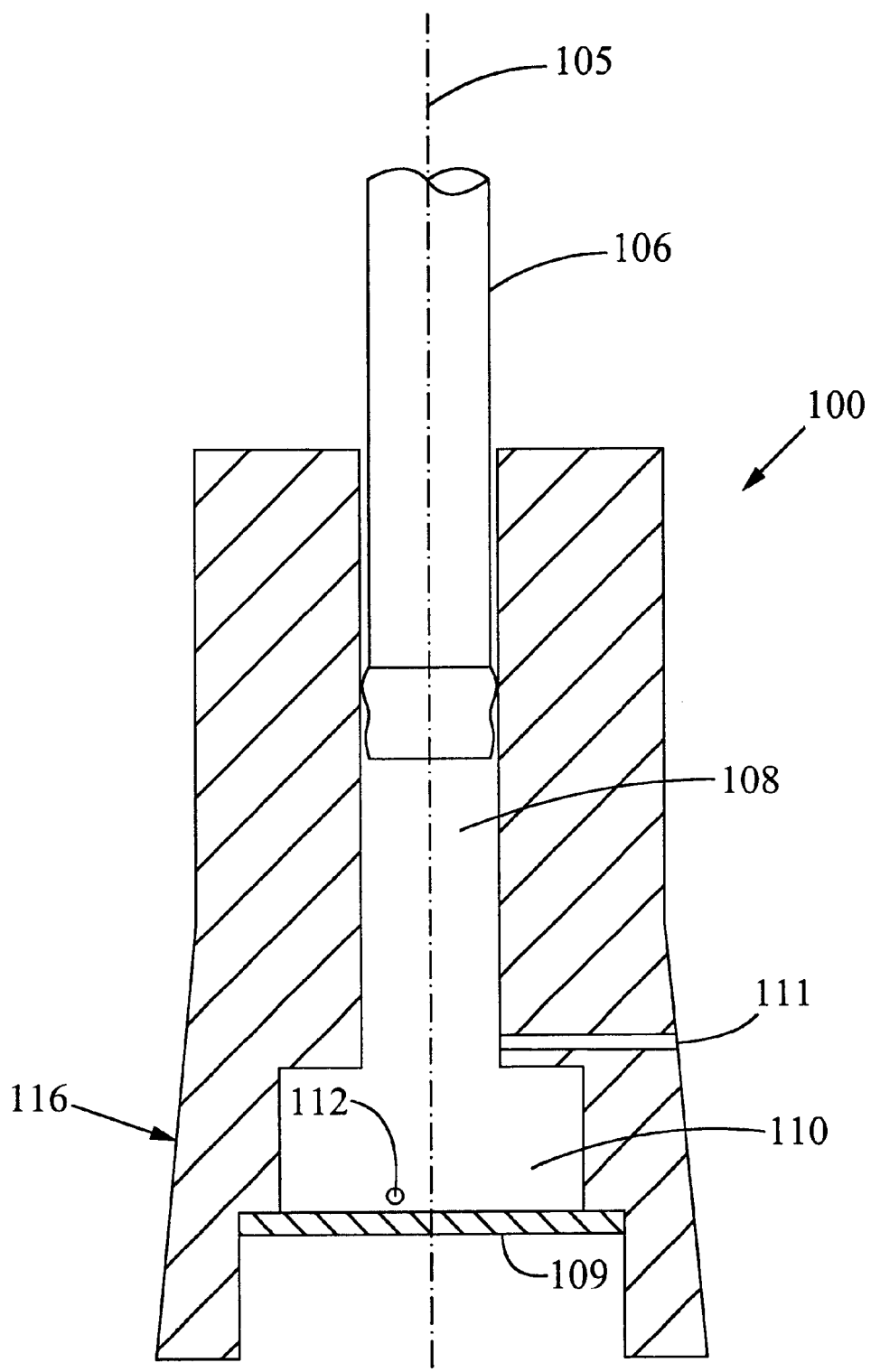
FIG. 11 is a cross-sectional view of a fluid control apparatus in the system of FIG. 10.

FIG. 10 shows another valve 100 which is rotatably coupled to a fluid control channel housing or block 102. A reaction vessel 104 is detachably coupled to the housing 102. The valve 100 is a generally tubular member with a longitudinal axis 105 as shown in FIG. 11. A piston 106 is movably connected to the valve 100 to change the volume of the fluid displacement chamber 108 as the piston 106 is moved up and down. A cover 109 is placed near the bottom of the valve 100. A fluid sample processing region 110 is disposed in the valve 100 and is in continuous fluidic communication with the fluid displacement chamber 108. The valve 100 includes a pair of apertures serving as a first port 111 and a second port 112, as best seen in FIG. 11. In the embodiment shown, the ports 111, 112 are angularly spaced by about 120°, but the spacing may be different in alternate embodiments. A crossover channel or groove 114 is formed on the external surface 116 of the valve 100 and extends generally in the longitudinal direction, as seen in FIG. 10. The two ports 111, 112 are disposed at different levels longitudinally offset from one another along the longitudinal axis 105, and the crossover groove 114 extends in the longitudinal direction of the axis 105 bridging the two levels of the ports 111, 112.

The housing 102 has an opening 118 for receiving the portion of the valve 100 having the ports 111, 112 and groove 114. The internal surface 120 around the opening 118 is shaped to cooperate with the external surface 116 of the valve 100. Although a gasket may be placed between the internal surface 120 and the external surface 116, a preferred embodiment employs tapered or conical surfaces 120, 116 that produce a sealing effect without the use of an additional gasket. The housing 102 includes a plurality of channels and ports and the valve 100 is rotatable around its axis 105 to allow the ports 111, 112 to be placed selectively in fluidic communication with the plurality of channels in the housing 102. Depending on which port is opened or closed and whether the piston 106 is moved upward or downward, the fluid flow in the valve 100 can change directions, and the ports 111, 112 can each switch from being an inlet port to an outlet port.

Figure 12A:
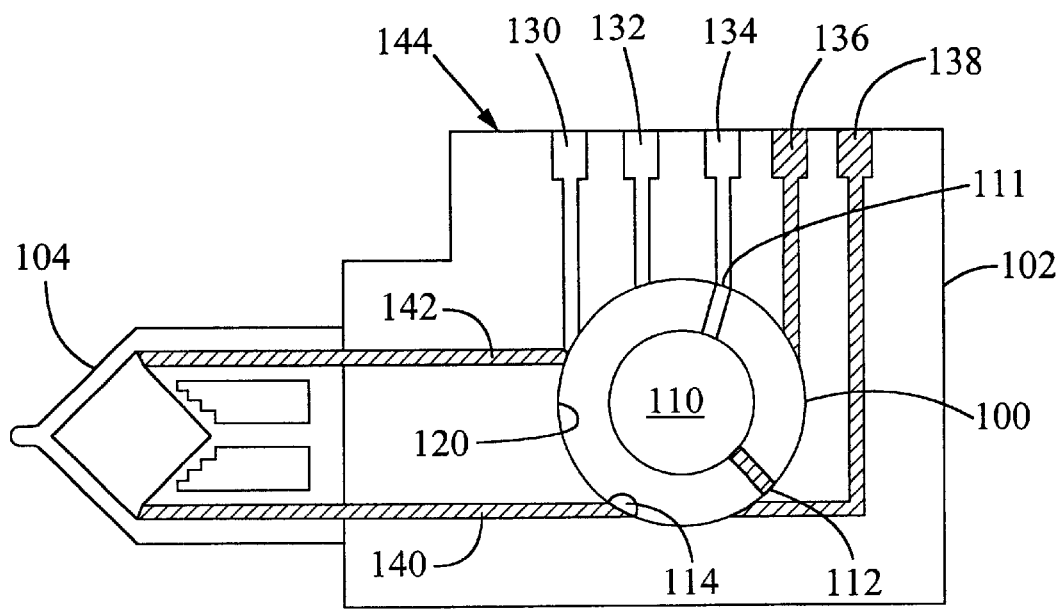
FIGS. 12A–12N are plan views illustrating a specific protocol for controlling and processing fluid using the fluid control and processing system of FIG. 10.
Figure 12B:
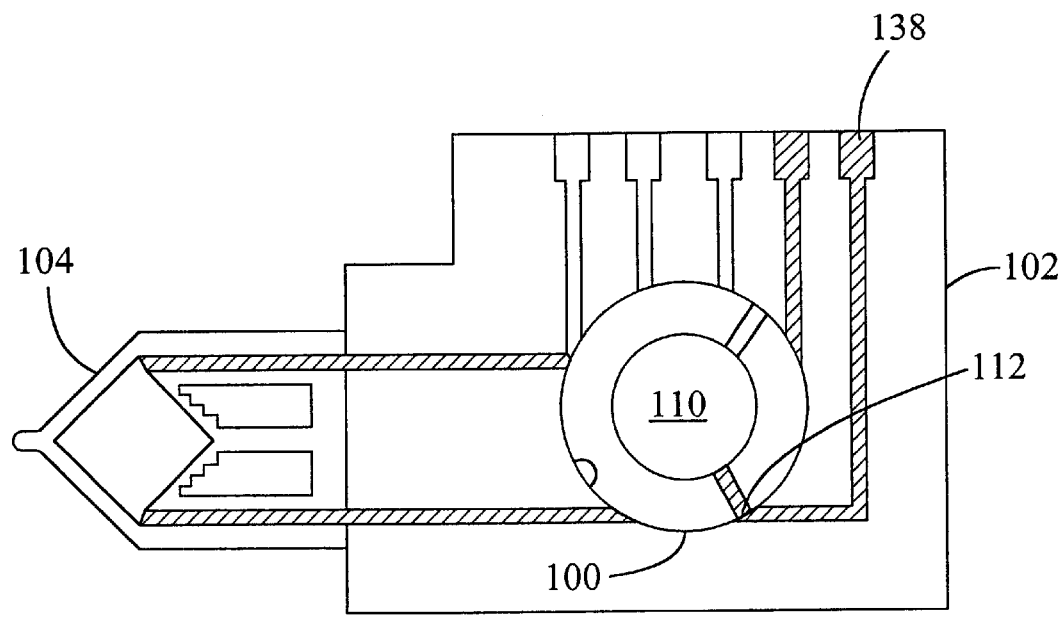
Figure 12C:
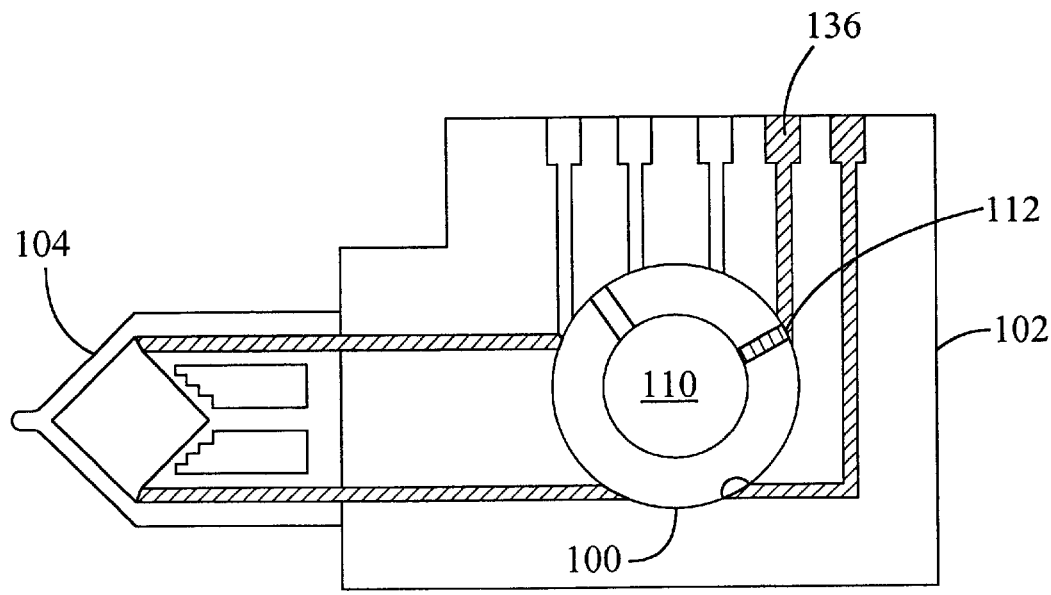
Figure 12D:
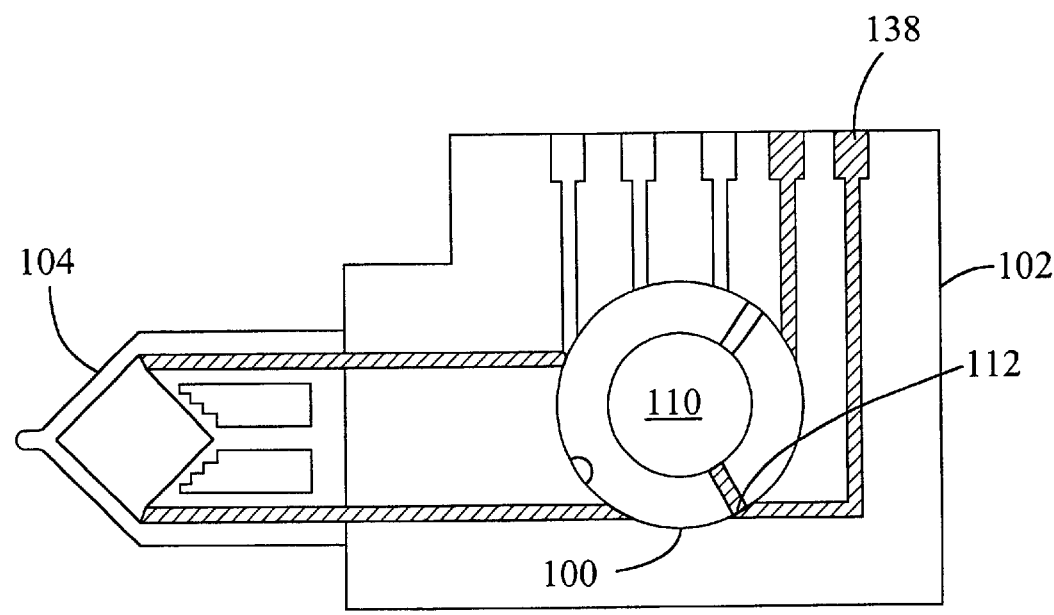
Figure 12E:
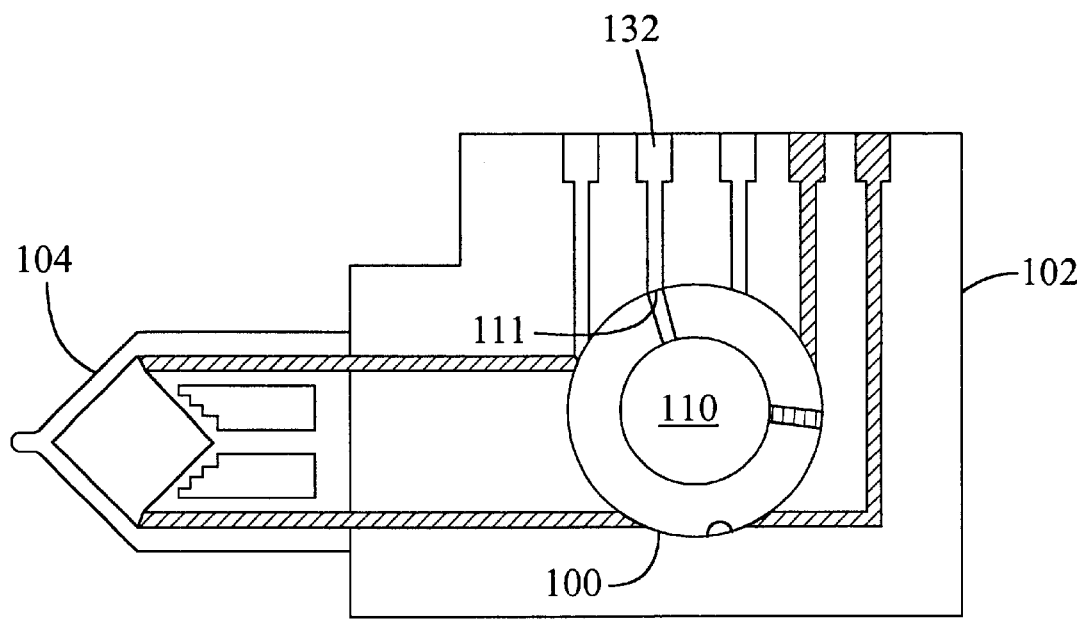
Figure 12F:
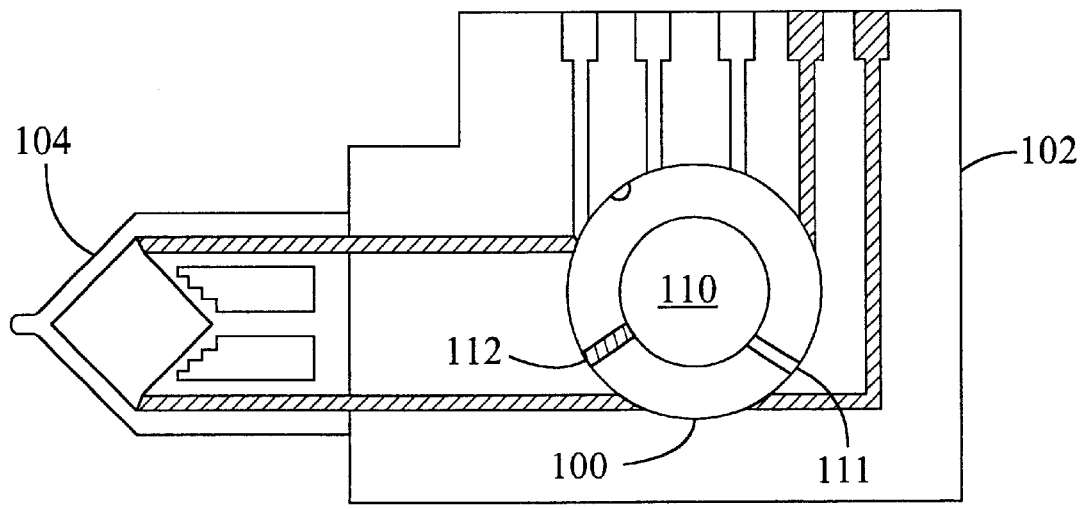
Figure 12G:
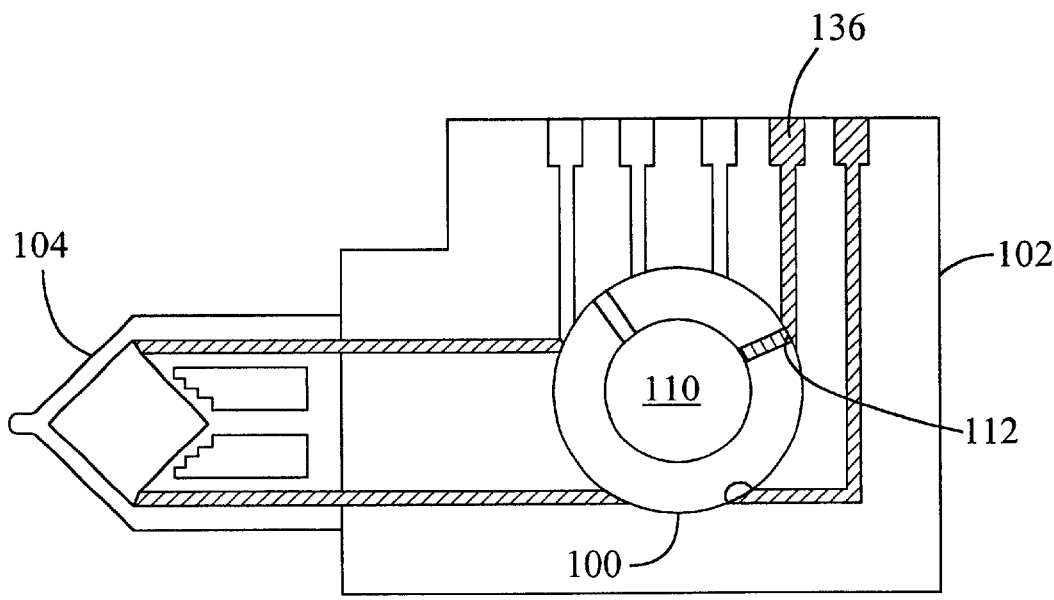
Figure 12H:
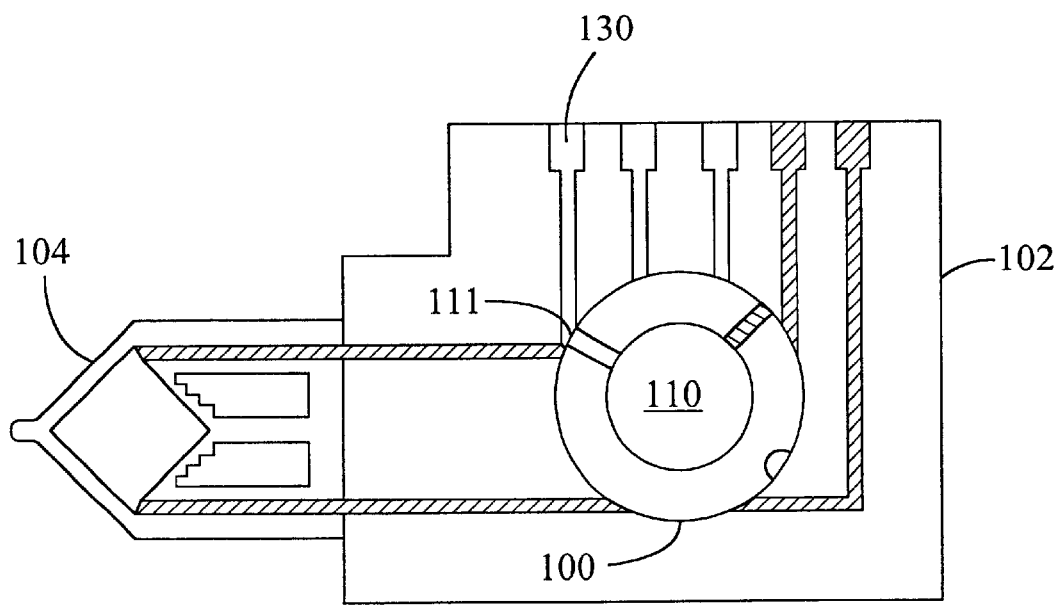
Figure 12I:
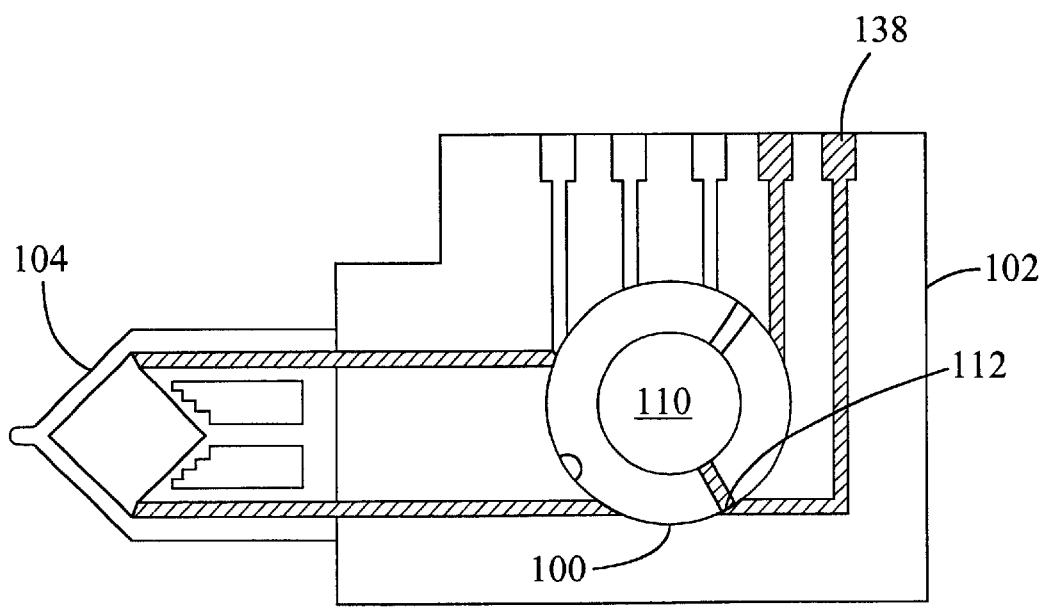
Figure 12J:
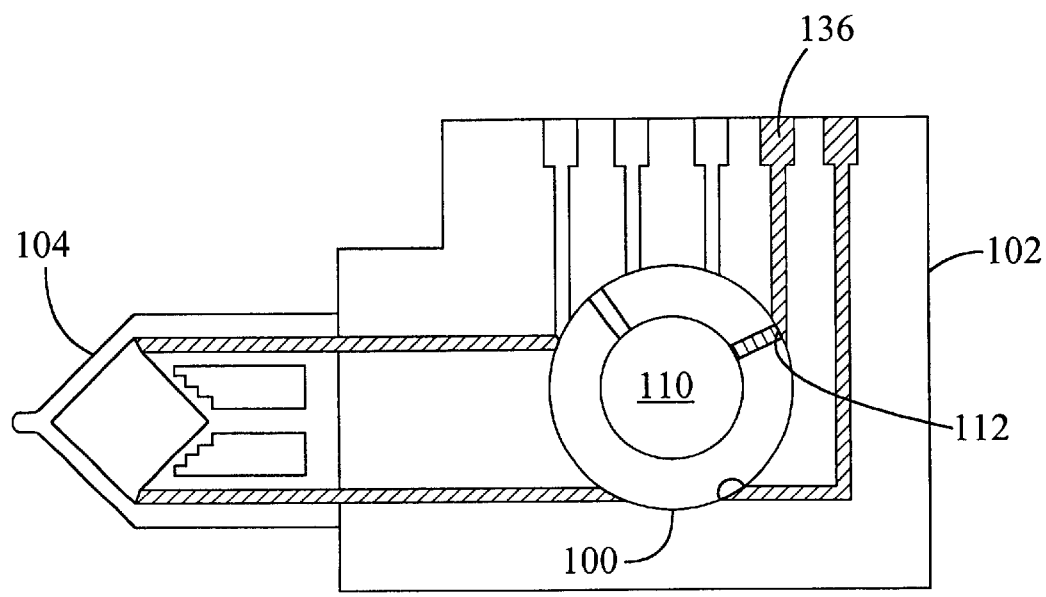
Figure 12K:
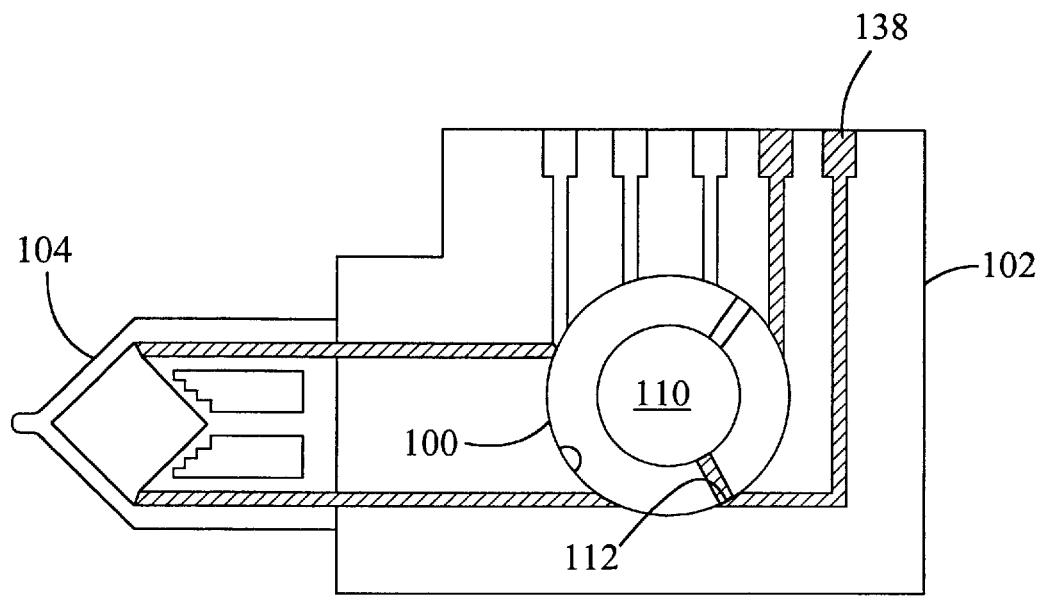
Figure 12L:
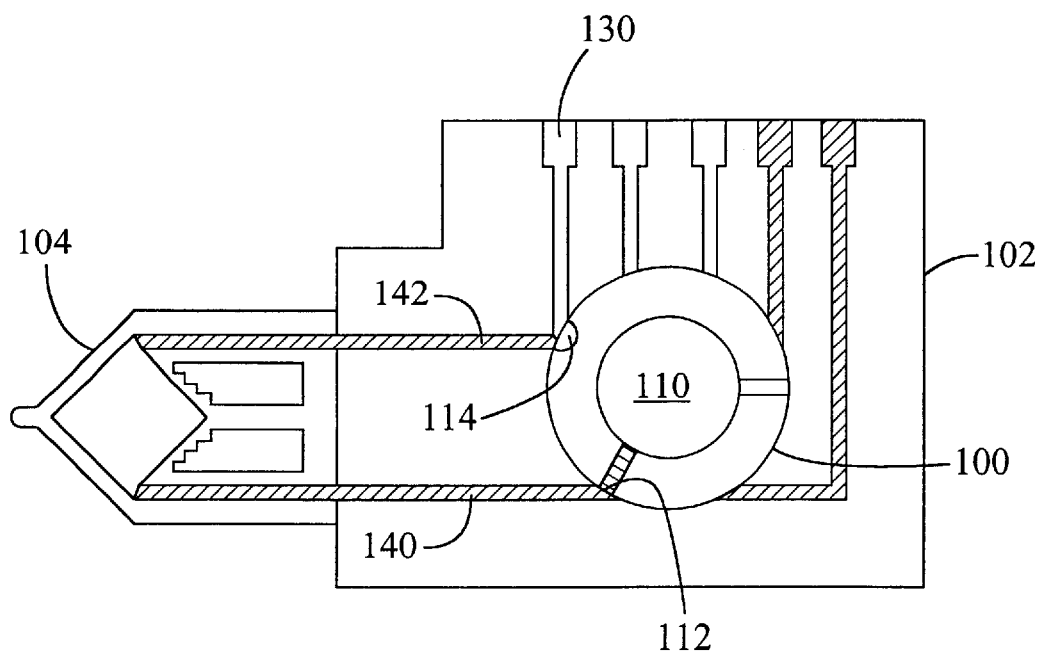
Figure 12M:
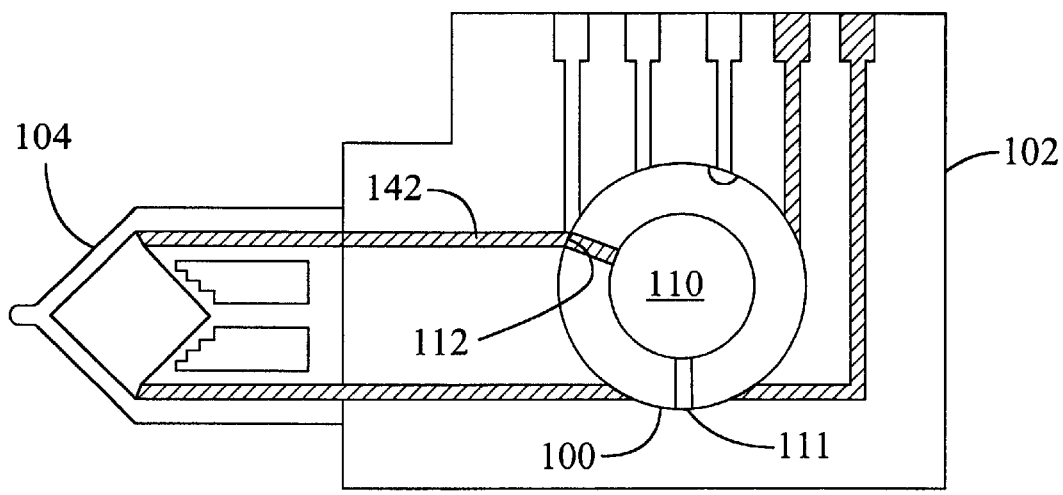
Figure 12N:
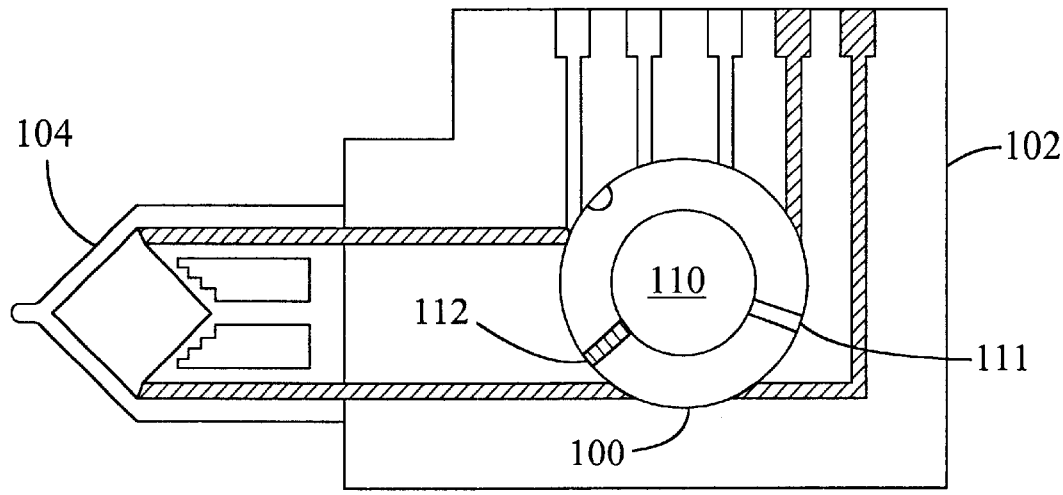

To demonstrate the fluid metering and distribution function of the valve 100, FIGS. 12A–12N illustrate the operation of the valve 100 for a specific protocol. As shown in FIG. 12A, the housing 102 includes a plurality of fluid channels. For convenience, the channels are labeled as follows: mastermix channel 130, lysate channel 132, sample channel 134, wash channel 136, waste channel 138, first branch 140, and second branch 142. The channels 130–138 extend from the internal surface 120 to one external surface 144 which is generally planar, and the branches 140, 142 extend from the internal surface 120 to another external surface 146 which is also generally planar (FIG. 10). When assembled, the first port 111 and the channels 130–134 lie on a first transverse plane that is perpendicular to the longitudinal axis 105, while the second port 112, the channels 136, 138, and the two branches 140, 142 lie on a second transverse plane that is perpendicular to the longitudinal axis 105. The second transverse plane is longitudinally offset from the first transverse plane. For convenience, the second port 112, the channels 136, 138, and the branches 140, 142 are shaded to indicate that they are longitudinally offset from the first port 111 and the channels 130–134. The crossover groove 114 extends longitudinally to bridge the offset between the first and second transverse planes. A chamber body 150 is connected to the housing 102 (FIG. 10), and includes the mastermix chamber, lysate chamber, sample chamber, wash chamber, and waste chamber that are respectively coupled fluidicly with the channels 130–138. The first and second branches 140, 142 are fluidicly coupled with the reaction vessel 104.

In FIG. 12A, the first port 111 is placed in fluidic communication with the sample channel 134 and the piston 106 is pulled upward to draw a fluid sample into the fluid displacement chamber 108 (FIG. 11). The valve 100 is then rotated to place the second port 112 in fluidic communication with the waste channel 138 and the piston 106 is pushed downward to drive the fluid sample from the displacement chamber 108 through the processing region 110, and out through the waste channel 138, as shown in FIG. 12B. These steps are typically repeated until an entire sample is processed through the processing region 110, for instance, to capture sample components on a trapping member such as a filter.

In FIG. 12C, the valve 100 is rotated to place the second port 112 in fluidic communication with the wash channel 136 to aspirate a wash fluid into the processing region 110 by pulling the piston 106 upward. The valve 100 is then rotated to place the second port 112 in fluidic communication with the waste channel 138 and the piston 106 is pushed downward to drive the wash fluid from the processing region 110 out through the waste channel 138. The above washing steps can be repeated as desired to remove unwanted residue inside the valve 100.

For lysing, the valve 100 is rotated to place the first port 111 in fluidic communication with the lysate channel 132 and the piston 106 is pulled upward to draw a lysate fluid into the fluid displacement chamber 108, as shown in FIG. 12E. In FIG. 12F, the valve 110 is rotated to close both ports 111, 112. The piston 106 is pushed downward to push the lysate fluid into the processing region 110 and to pressurize the lysate fluid and the sample components captured in the fluid sample processing region 110. Additional energy may be applied to the mixture in the processing region 110 including, for instance, sonic energy transmitted into the processing region 110 by operatively coupling a sonic member with the cover 109 (FIG. 11).

In FIG. 12G, a desired preset amount of wash fluid is aspirated into the processing region 110 from the wash channel 136 through the second port 112 to dilute the mixture. The valve 100 is then rotated to place the first port 111 in fluidic communication with the mastermix channel 130 to discharge a preset amount of the mixture from the processing region 110 to the mastermix chamber, as shown in FIG. 12H. The piston 106 is moved up and down to agitate and mix the mixture by toggling. The balance of the mixture is discharged through the second port 112 to the waste channel 138, as shown in FIG. 12I. Another wash is performed by drawing a wash fluid from the wash channel 136 through the second port 112 into the processing region 110 (FIG. 12J), and discharging the wash fluid from the processing region 110 through the second port 112 to the waste channel 138 (FIG. 12K).

In FIG. 12L, the valve 100 is rotated to place the second port 112 in fluidic communication with the first branch 140 coupled to the reaction vessel 104, while the second branch 142 which is coupled to the reaction vessel 104 is placed in fluidic communication with the crossover groove 114. The second branch 142 is longitudinal offset from the mastermix channel 130. In the position as shown in FIG. 12L, the crossover groove 114 extends longitudinally to bridge the offset between the second branch 142 and the mastermix channel 130 to place them in fluidic communication with one another. As a result, the fluid sample processing region 110 is in fluidic communication, through the first branch 140, the reaction vessel 104, the second branch 142, and the crossover groove 114, with the mastermix channel 130.

By pulling the piston 106 upward, the mixture in the mastermix chamber is drawn from the mastermix channel 130 through the crossover groove 114 and the second branch 142 into the reaction vessel 104. The valve 100 is then rotated to place the second port 112 in fluidic communication with the second branch 142 and to close the first port 111, as shown in FIG. 12M. The piston 106 is pushed downward to pressurize the mixture inside the reaction vessel 104. In FIG. 12N, the valve 100 is rotated to close the ports 111, 112 and isolate the reaction vessel 104. The reaction vessel 104 may be inserted into a thermal reaction chamber for performing nucleic acid amplification and/or detection.

As illustrated in the above embodiments, the fluid control and processing system is advantageously a fully contained system that is versatile and adaptable. The fluid displacement chamber is the motivating force for moving fluid in the system. By maintaining a continuous fluidic communication between the fluid displacement chamber and the fluid sample processing region, the motivating force for moving fluid in the system is fluidicly coupled to the processing region at all times. The fluid displacement chamber (motivating force) also acts as a temporary storage area for the fluid being driven through the system. A single motivating force is used to move fluid through the system. While the embodiments shown employ a moving piston in the fluid displacement chamber as the motivating force, other mechanisms may be used including, e.g., pneumatic pump mechanisms or the like which use pressure as the motivating force without a change in volume of the fluid displacement chamber. The inlet or outlet side of the fluid sample processing region can address any of the chambers to permit random access to reagents and other fluids. Complex protocols can be programmed relatively easily into a computer controller and then executed using the versatile fluid control and processing system. A myriad of different protocols can be performed using a single platform.

In the embodiments shown, the fluid control occurs by addressing a pair of ports in the valve to place only one port at a time selectively in fluidic communication with the chambers. This is accomplished by keeping the pair of ports out of phase relative to the chambers. A crossover or bypass channel provides additional fluid control capability (e.g., allowing convenient filling and emptying of the reaction vessel within the closed system). Of course, different porting schemes may be used to achieve the desired fluid control in other embodiments. Moreover, while the embodiments shown each include a single fluid sample processing region in the valve body, additional processing regions can be located in the valve body if desired. Generally, the valve body needs (n+1) ports per n processing regions.

The use of a single valve produces high manufacturing yields due to the presence of only one failure element. The concentration of the fluid control and processing components results in a compact apparatus (e.g., in the form of a small cartridge) and facilitates automated molding and assembly. As discussed above, the system advantageously includes dilution and mixing capability, intermediate wash capability, and positive pressurization capability. The fluid paths inside the system are normally closed to minimize contamination and facilitate containment and control of fluids within the system. The reaction vessel is conveniently detachable and replaceable, and may be disposable in some embodiments.

The components of the fluid control and processing system may be made of a variety of materials that are compatible with the fluids being used. Examples of suitable materials include polymeric materials such as polypropylene, polyethylene, polycarbonate, acrylic, or nylon. The various chambers, channels, ports, and the like in the system may have various shapes and sizes.

The above-described arrangements of apparatus and methods are merely illustrative of applications of the principles of this invention and many other embodiments and modifications may be made without departing from the spirit and scope of the invention as defined in the claims.

Figure 13:
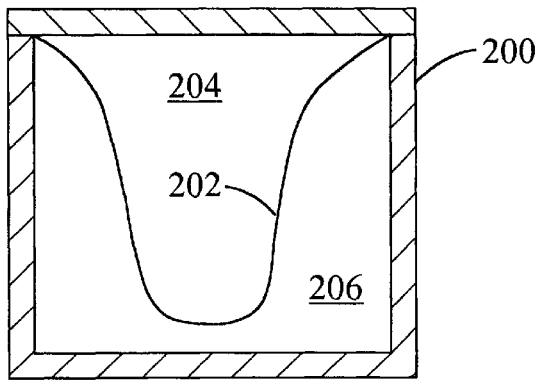
FIG. 13 is a cross-sectional view of a soft-walled chamber.

For instance, FIG. 13 shows a soft-walled chamber 200 that may be incorporated into the fluid control and processing system. Typically, an on-board reagent style cartridge requires a total fluid volume of at least twice the total volume of reagents and sample combined in rigid systems.

The use of soft-walled chambers can reduce the required volume. These chambers have flexible walls, and can typically be formed using films and thermoforming. An added advantage of soft walls is that venting need not be provided if the walls are sufficiently flexible to allow them to collapse when the chamber is emptied. In FIG. 13, a flexible sidewall 202 separates a reagent chamber 204 and a waste chamber 206. Because the waste is composed of the sample and reagents, the volume required for waste is no more than the sum of the sample and reagents. The reagent chamber 204 contracts while the waste chamber 206 expands, and vice versa. This can be a closed system with no connection to the exterior. The configuration can reduce the overall size of the cartridge, and can allow fast change-overs of chamber volumes. It can also eliminate venting, and can cut costs by reducing the number of platforms that would otherwise need to be built with hard tooling. In one embodiment, at least two of the plurality of chambers in the system are separated by a flexible wall to permit change-over of chamber volumes between the chambers.

Figure 14:
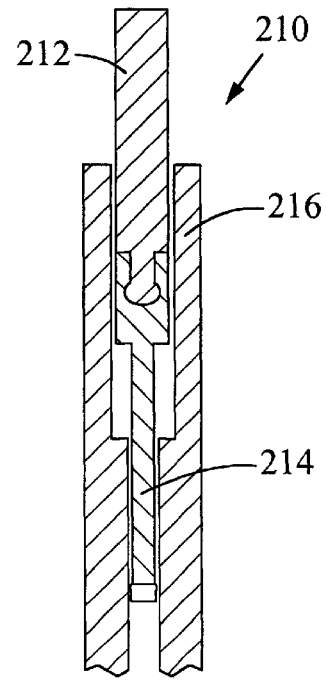
FIG. 14 is a cross-sectional view of a piston assembly.

FIG. 14 shows a piston assembly 210 including a piston rod 212 connected to a piston shaft 214 having a smaller cross-section than the rod 212 for driving small amounts of fluids. The thin piston shaft 214 may bend under an applied force if it is too long. The piston rod 212 moves along the upper portion of the barrel or housing 216, while the piston shaft 214 moves along the lower portion of the barrel 216. The movement of the piston rod 212 guides the movement of the piston shaft 214, and absorbs much of the applied force so that very little bending force is transmitted to the thin piston shaft 214.

Figure 15:
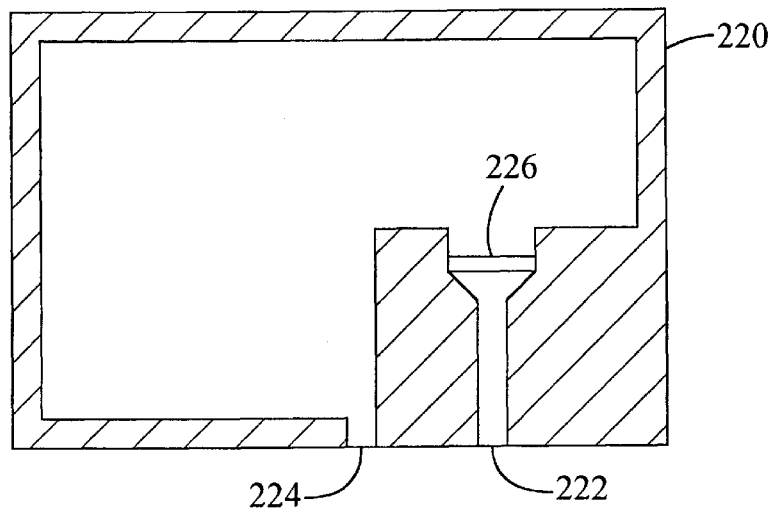
FIG. 15 is a cross-sectional view of a side filtering chamber.

FIG. 15 shows a side chamber 220 that may be incorporated into the system. The side chamber 220 includes an inlet port 222 and an outlet port 224. In this example, the side chamber 220 includes a filter 226 disposed at the inlet port 222. Fluid is directed to flow via the inlet port 222 into the side chamber 220 and out via the outlet port 224 for side filtering. This allows filtering of a fluid sample or the like using the fluid control system of the invention. The fluid may be recirculated to achieve better filtering by the filter 226. This prefiltering is useful to remove particles before introducing the fluid into the main chambers of the system to prevent clogging. The use of a side chamber is advantageous, for instance, to avoid contaminating the valve and the main chambers in the system.

The scope of the invention should, therefore, be determined not with reference to the above description, but instead should be determined with reference to the appended claims along with their full scope of equivalents.

What is claimed is:

1. A fluid control and processing system comprising:
   a housing having a plurality of chambers; and
   a valve body including a fluid sample processing region continuously coupled fluidicly with a fluid displacement region, the fluid displacement region being depressurizable to draw fluid into the fluid displacement region and pressurizable to expel fluid from the fluid displacement region, the valve body including a plurality of external ports, the fluid sample processing region including a plurality of fluid processing ports each fluidicly coupled with one of the external ports, the fluid displacement region being fluidicly coupled with at least one of the external ports, and the valve body being adjustable with respect to the housing to allow the external ports to be placed selectively in fluidic communication with the plurality of chambers.

2. The system of claim 1 wherein the valve body is adjustable with respect to the housing to place one external port at a time in fluidic communication with one of the plurality of chambers.

3. The system of claim 1 wherein the valve body is adjustable with respect to the housing to place at least two of the external ports in fluidic communication with any of the plurality of chambers at a time.

4. The system of claim 1 wherein the fluid displacement region is fluidicly coupled to a fluid displacement channel in the valve body and one of the fluid processing ports is fluidicly coupled to a fluid processing channel in the valve body, the fluid displacement channel and the fluid processing channel being fluidicly coupled with one external port.

5. The system of claim 1 wherein the plurality of fluid processing ports are each continuously coupled fluidicly with at least one of the external ports.

6. The system of claim 1 wherein the fluid sample processing region is disposed between the fluid displacement region and at least one external port so that fluid flow between the fluid displacement region and the at least one external port passes through the fluid sample processing region.

7. The system of claim 1 wherein the external ports are disposed on one external port surface of the valve body.

8. The system of claim 7 wherein the external port surface is generally planar.

9. The system of claim 8 wherein the valve body is rotatable around an axis and relative to the plurality of chambers to allow the external ports to be placed selectively in fluidic communication with the plurality of chambers, the axis being perpendicular to the external port surface, and the external ports being spaced from the axis by a common radius.

10. The system of claim 1 wherein the fluid displacement region is depressurizable by increasing in volume and is pressurizable by decreasing in volume.

11. The system of claim 10 further comprising a fluid displacement member disposed in the fluid displacement region, the fluid displacement member being movable to adjust the volume of the fluid displacement region.

12. The system of claim 11 wherein the fluid displacement member comprises a piston movable in a linear direction in the fluid displacement region.

13. The system of claim 11 wherein the fluid displacement member comprises a piston shaft which is connected to a distal portion of a piston rod for driving the piston shaft to move inside the fluid displacement region, the piston shaft being smaller in cross-section than the piston rod.

14. The system of claim 1 further comprising an energy transmitting member operatively coupled with the fluid sample processing region for transmitting energy thereto to process fluid contained therein.

15. The system of claim 14 further comprising a cover disposed between the fluid sample processing region and the energy transmitting member.

16. The system of claim 15 wherein the cover comprises a flexible film.

17. The system of claim 16 wherein the energy transmitting member comprises a sonic member for contacting the cover to transmit sonic energy through the cover into the fluid sample processing region.

18. The system of claim 1 wherein the valve body includes a crossover channel, the valve body being adjustable with respect to the housing to place the crossover channel in fluidic communication with an aspiration chamber and a source chamber to permit aspiration of a fluid from the source chamber through the crossover channel to the aspiration chamber.

19. The system of claim 18 wherein the external ports are disposed on a generally planar external port surface which is perpendicular to an axis, the external ports being rotatable around the axis relative to the plurality of chambers to place the external ports selectively in fluidic communication with the plurality of chambers, and wherein the crossover channel comprises a crossover groove on the external port surface.

20. The system of claim 19 wherein the external ports are disposed within a range of external port radii from the axis and the crossover groove is disposed within a range of crossover groove radii from the axis, the range of external port radii and the range of crossover groove radii being non-overlapping.

21. The system of claim 20 wherein the crossover groove is a circular arc lying on a common crossover groove radius from the axis.

22. The system of claim 20 wherein the external ports are spaced from the axis by a common radius.

23. The system of claim 1 wherein the external ports are disposed on an external port surface that is generally conical relative to a longitudinal axis of rotation of the valve body, the external ports including a first external port angularly spaced from a second external port about the longitudinal axis.

24. The system of claim 23 wherein the valve body is rotatable around the longitudinal axis and relative to the plurality of chambers to allow the external ports to be placed selectively in fluidic communication with the plurality of chambers, wherein the first external port lies on a first transverse plane which is perpendicular to the longitudinal axis and which is longitudinally offset in the direction of the longitudinal axis from a second transverse plane which is perpendicular to the longitudinal axis, wherein the second external port lies on the second plane.

25. The system of claim 24 wherein the valve body includes a crossover groove disposed on the external port surface.

26. The system of claim 25 wherein the crossover groove extends longitudinally between the first transverse plane and the second transverse plane.

27. The system of claim 1 wherein the fluid sample processing region comprises an active member selected from the group consisting of a microfluidic chip, a solid phase material, a filter, a filter stack, an affinity matrix, a magnetic separation matrix, a size exclusion column, and a capillary tube.

28. The system of claim 1 wherein at least two of the plurality of chambers are separated by a flexible wall to permit change-over of chamber volumes between the chambers.

29. The system of claim 1 wherein the plurality of chambers comprise a side chamber including an inlet port, an outlet port, and a filter disposed at the inlet port.

30. A fluid control and processing system comprising:
a housing having a plurality of chambers; and
a valve body including a fluid sample processing region continuously coupled fluidicly with a fluid displacement region, the fluid displacement region being depressurizable to draw fluid into the fluid displacement region and pressurizable to expel fluid from the fluid displacement region, the valve body including a plurality of external ports, the fluid sample processing region being fluidicly coupled with at least two of the external ports, the fluid displacement region being fluidicly coupled with at least one of the external ports, and the valve body being adjustable with respect to the housing to place at least one of the external ports selectively in fluidic communication with the plurality of chambers.

31. The system of claim 30 wherein the valve body is adjustable with respect to the housing to place at most one external port at a time in fluidic communication with one of the plurality of chambers.

32. The system of claim 30 wherein the valve body is adjustable with respect to the housing to close the external ports so that the fluid displacement region and the processing region are fluidicly isolated from the chambers.

33. The system of claim 30 wherein the fluid sample processing region comprises a trapping member for trapping components of a fluid sample.

34. A method for controlling fluid flow between a valve and a plurality of chambers, the valve including a plurality of external ports and a fluid displacement region continuously coupled fluidicly with a fluid sample processing region which is fluidicly coupled with at least two of the external ports, the method comprising:
adjusting the valve with respect to the plurality of chambers to place the external ports selectively in fluidic communication with the plurality of chambers.

35. The method of claim 34 wherein the valve is adjusted to close the external ports so that the valve is fluidicly isolated from the chambers.

36. The method of claim 35 further comprising pressurizing the fluidic displacement region and the fluid sample processing region.

37. The method of claim 34 wherein the valve is adjusted to place one external port In fluidic communication with one of the chambers, and further comprising depressurizing the fluid displacement region to aspirate fluid from the chamber into the valve.

38. The method of claim 34 wherein the valve is adjusted to place one external port in fluidic communication with one of the chambers, and further comprising pressurizing the fluid displacement region to expel fluid from the valve into the, chamber.

39. The method of claim 34 wherein the valve includes a crossover channel, and wherein the valve is adjusted to place one external port in fluidic communication with a first chamber and to place the crossover channel in fluidic communication with the first chamber and a second chamber.

40. The method of claim 39 further comprising depressurizing the fluid displacement region to aspirate fluid from the second chamber through the crossover channel to the first chamber.

41. The method of claim 34 further comprising transmitting energy into the fluid sample processing region.

42. The system of claim 30 wherein the fluid displacement region is fluidicly coupled to a fluid displacement channel in the valve body and one of the fluid processing ports is fluidicly coupled to a fluid processing channel in the valve body, the fluid displacement channel and the fluid processing channel being fluidicly coupled with one external port.

43. The system of claim 30 wherein the fluid sample processing region includes a plurality of fluid processing ports each continuously coupled fluidicly with at least one of the external ports.

44. The system of claim 30 wherein the fluid sample processing region is disposed between the fluid displacement region and at least one external port so that fluid flow between the fluid displacement region and the at least one external port passes through the fluid sample processing region.

45. The system of claim 30 wherein the external ports are disposed on one external port surface of the valve body.

46. The system of claim 45 wherein the external port surface is generally planar.

47. The system of claim 46 wherein the valve body is rotatable around an axis and relative to the plurality of chambers to allow the external ports to be placed selectively in fluidic communication with the plurality of chambers, the axis being perpendicular to the external port surface, and the external ports being spaced from the axis by a common radius.

48. The system of claim 30 wherein the fluid displacement region is depressurizable by increasing in volume and is pressurizable by decreasing in volume.

49. The system of claim 48 further comprising a fluid displacement member disposed in the fluid displacement region, the fluid displacement member being movable to adjust the volume of the fluid displacement region.

50. The system of claim 49 wherein the fluid displacement member comprises a piston movable in a linear direction in the fluid displacement region.

51. The system of claim 49 wherein the fluid displacement member comprises a piston shaft which is connected to a distal portion of a piston rod for driving the piston shaft to move inside the fluid displacement region, the piston shaft being smaller in cross-section than the piston rod.

52. The system of claim 30 further comprising an energy transmitting member operatively coupled with the fluid sample processing region for transmitting energy thereto to process fluid contained therein.

53. The system of claim 52 further comprising a cover disposed between the fluid sample processing region and the energy transmitting member.

54. The system of claim 53 wherein the cover comprises a flexible film.

55. The system of claim 54 wherein the energy transmitting member comprises a sonic member for contacting the cover to transmit sonic energy through the cover into the fluid sample processing region.

56. The system of claim 30 wherein the valve body includes a crossover channel, the valve body being adjustable with respect to the housing to place the crossover channel in fluidic communication with an aspiration chamber and a source chamber to permit aspiration of a fluid from the source chamber through the crossover channel to the aspiration chamber.

57. The system of claim 56 wherein the external ports are disposed on a generally planar external port surface which is perpendicular to an axis, the external ports being rotatable around the axis relative to the plurality of chambers to place the external ports selectively in fluidic communication with the plurality of chambers, and wherein the crossover channel comprises a crossover groove on the external port surface.

58. The system of claim 57 wherein the external ports are disposed within a range of external port radii from the axis and the crossover groove is disposed within a range of crossover groove radii from the axis, the range of external port radii and the range of crossover groove radii being non-overlapping.

59. The system of claim 58 wherein the crossover groove is a circular arc lying on a common crossover groove radius from the axis.

60. The system of claim 58 wherein the external ports are spaced from the axis by a common radius.

61. The system of claim 30 wherein the external ports are disposed on an external port surface that is generally conical relative to a longitudinal axis of rotation of the valve body, the external ports including a first external port angularly spaced from a second external port about the longitudinal axis.

62. The system of claim 61 wherein the valve body is rotatable around the longitudinal axis and relative to the plurality of chambers to allow the external ports to be placed selectively in fluidic communication with the plurality of chambers, wherein the first external port lies on a first transverse plane which is perpendicular to the longitudinal axis and which is longitudinally offset in the direction of the longitudinal axis from a second transverse plane which is perpendicular to the longitudinal axis, wherein the second external port lies on the second plane.

63. The system of claim 62 wherein the valve body includes a crossover groove disposed on the external port surface.

64. The system of claim 63 wherein the crossover groove extends longitudinally between the first transverse plane and the second transverse plane.

65. The system of claim 30 wherein the fluid sample processing region comprises an active member selected from the group consisting of a microfluidic chip, a solid phase material, a filter, a filter stack, an affinity matrix, a magnetic separation matrix, a size exclusion column, and a capillary tube.

66. The system of claim 30 wherein at least two of the plurality of chambers are separated by a flexible wall to permit change-over of chamber volumes between the chambers.

67. The system of claim 30 wherein the plurality of chambers comprise a side chamber including an inlet port, an outlet port, and a filter disposed at the inlet port.

68. A fluid control and processing system for controlling fluid flow among a plurality of chambers, the system comprising:
a body including a fluid sample processing region continuously coupled fluidicly with a fluid displacement region, the fluid displacement region being depressurizable to draw fluid into the fluid displacement region and pressurizable to expel fluid from the fluid displacement region, the body including a plurality of external ports, the fluid sample processing region including a plurality of fluid processing ports each fluidicly coupled with one of the external ports, the fluid displacement region being fluidicly coupled with at least one of the external ports, and the body being rotatably adjustable around an axis and relative to the plurality of chamber to allow the external ports to be placed selectively in fluidic communication with the plurality of chambers.

69. The system of claim 68 wherein the body is adjustable with respect to the plurality of chambers to place one external port at a time in fluidic communication with one of the plurality of chambers.

70. The system of claim 68 wherein the body is adjustable with respect to the plurality of chambers to place at least two of the external ports in fluidic communication with any of the plurality of chambers at a time.

71. The system of claim 68 wherein: the fluid displacement region is fluidicly coupled to a fluid displacement channel in the body and one of the fluid processing ports is fluidicly coupled to a fluid processing channel in the body, the fluid displacement channel and the fluid processing channel being fluidicly coupled with one external port.

72. The system of claim 68 wherein the plurality of fluid processing ports are each continuously coupled fluidicly with at least one of the external ports.

73. The system of claim 68 wherein the fluid sample processing region is disposed between the fluid displacement region and at least one external port so that fluid flow between the fluid displacement region and the at least one external port passes through the fluid sample processing region.

74. The system of claim 68 wherein the external ports are disposed on one external port surface of the body.

75. The system of claim 74 wherein the external port surface is generally planar.

76. The system of claim 75 wherein the axis is perpendicular to the external port surface, and wherein the external ports are spaced from the axis by a common radius.

77. The system of claim 68 wherein the fluid displacement region is depressurizable by increasing in volume and is pressurizable by decreasing in volume.

78. The system of claim 77 further comprising a fluid displacement member disposed in the fluid displacement region, the fluid displacement member being movable to adjust the volume of the fluid displacement region.

79. The system of claim 78 wherein the fluid displacement member comprises a piston movable in a linear direction in the fluid displacement region.

80. The system of claim 78 wherein the fluid displacement member comprises a piston shaft which is connected to a distal portion of a piston rod for driving the piston shaft to move inside the fluid displacement region, the piston shaft being smaller in cross-section than the piston rod.

81. The system of claim 68 further comprising an energy transmitting member operatively coupled with the fluid sample processing region for transmitting energy thereto to process fluid contained therein.

82. The system of claim 81 further comprising a cover disposed between the fluid sample processing region and the energy transmitting member.

83. The system of claim 82 wherein the cover comprises a flexible film.

84. The system of claim 83 wherein the energy transmitting member comprises a sonic member for contacting the cover to transmit sonic energy through the cover into the fluid sample processing region.

85. The system of claim 68 wherein the body includes a crossover channel, the body being adjustable with respect to the plurality of chambers to place the crossover channel in fluidic communication with an aspiration chamber and a source chamber to permit aspiration of a fluid from the source chamber through the crossover channel to the aspiration chamber.

86. The system of claim 85 wherein the external ports are disposed on a generally planar external port surface which is perpendicular to the axis, the external ports being rotatable around the axis relative to the plurality of chambers to place the external ports selectively in fluidic communication with the plurality of chambers, and wherein the crossover channel comprises a crossover groove on the external port surface.

87. The system of claim 86 wherein the external ports are disposed within a range of external port radii from the axis and the crossover groove is disposed within a range of crossover groove radii from the axis, the range of external port radii and the range of crossover groove radii being non-overlapping.

88. The system of claim 87 wherein the crossover groove is a circular arc lying on a common crossover groove radius from the axis.

89. The system of claim 87 wherein the external ports are spaced from the axis by a common radius.

90. The system of claim 68 wherein the external ports are disposed on an external port surface that is generally conical relative to the axis of rotation of the body, the external ports including a first external port angularly spaced from a second external port about the axis.

91. The system of claim 90 wherein the first external port lies on a first transverse plane which is perpendicular to the axis and which is longitudinally offset in the direction of the axis from a second transverse plane which is perpendicular to the axis, wherein the second external port lies on the second plane.

92. The system of claim 91 wherein the body includes a crossover groove disposed on the external port surface.

93. The system of claim 92 wherein the crossover groove extends longitudinally between the first transverse plane and the second transverse plane.

94. The system of claim 68 wherein the fluid sample processing region comprises an active member selected from the group consisting of a microfluidic chip, a solid phase material, a filter, a filter stack, an affinity matrix, a magnetic separation matrix, a size exclusion column, and a capillary tube.

95. The system of claim 68 wherein at least two of the plurality of chambers are separated by a flexible wall to permit change-over of chamber volumes between the chambers.

96. The system of claim 68 wherein the plurality of chambers comprise a side chamber including an inlet port, an outlet port, and a filter disposed at the inlet port.

97. A fluid control and processing system for controlling fluid flow among a plurality of chambers, the system comprising:

a body including a fluid sample processing region continuously coupled fluidicly with a fluid displacement region, the fluid displacement region being depressurizable to draw fluid into the fluid displacement region and pressurizable to expel fluid from the fluid displacement region, the body including a plurality of external ports, the fluid sample processing region being fluidicly coupled with at least two of the external ports, the fluid displacement region being fluidicly coupled with at least one of the external ports, and the body being rotatobly adjustable around an axis and relative to the plurality of chambers to place at least one of the external ports selectively in fluidic communication with the plurality of chambers.

98. The system of claim 97 wherein the body is adjustable with respect to the plurality of chambers to place at most one external port at a time in fluidic communication with one of the plurality of chambers.

99. The system of claim 97 wherein the body is adjustable with respect to the plurality of chambers to close the external ports so that the fluid displacement region and the processing region are fluidicly isolated from the chambers.

100. The system of claim 97 wherein the fluid sample processing region comprises a trapping member for trapping components of a fluid sample.

101. The system of claim 97 wherein the fluid displacement region is fluidicly coupled to a fluid displacement channel in the body and one of the fluid processing ports is fluidicly coupled to a fluid processing channel in the body, the fluid displacement channel and the fluid processing channel being fluidicly coupled with one external port.

102. The system of claim 97 wherein the plurality of fluid processing ports are each continuously coupled fluidicly with at least one of the external ports.

103. The system of claim 97 wherein the fluid sample processing region is disposed between the fluid displacement region and at least one external port so that fluid flow between the fluid displacement region and the at least one external port passes through the fluid sample processing region.

104. The system of claim 97 wherein the external ports are disposed on one external port surface of the body.

105. The system of claim 104 wherein the external port surface is generally planar.

106. The system of claim 105 wherein the axis is perpendicular to the external port surface, and wherein the external ports are spaced from the axis by a common radius.

107. The system of claim 97 wherein the fluid displacement region is depressurizable by increasing in volume and is pressurizable by decreasing in volume.

108. The system of claim 107 further comprising a fluid displacement member disposed in the fluid displacement region, the fluid displacement member being movable to adjust the volume of the fluid displacement region.

109. The system of claim 108 wherein the fluid displacement member comprises a piston movable in a linear direction in the fluid displacement region.

110. The system of claim 108 wherein the fluid displacement member comprises a piston shaft which is connected to a distal portion of a piston rod for driving the piston shaft to move inside the fluid displacement region, the piston shaft being smaller in cross-section than the piston rod.

111. The system of claim 97 further comprising an energy transmitting member operatively coupled with the fluid sample processing region for transmitting energy thereto to process fluid contained therein.

112. The system of claim 111 further comprising a cover disposed between the fluid sample processing region and the energy transmitting member.

113. The system of claim 112 wherein the cover comprises a flexible film.

114. The system of claim 113 wherein the energy transmitting member comprises a sonic member for contacting the cover to transmit sonic energy through the cover into the fluid sample processing region.

115. The system of claim 97 wherein the body includes a crossover channel, the body being adjustable with respect to the plurality of chambers to place the crossover channel in fluidic communication with an aspiration chamber and a source chamber to permit aspiration of a fluid from the source chamber through the crossover channel to the aspiration chamber.

116. The system of claim 115 wherein the external ports are disposed on a generally planar external port surface which is perpendicular to the axis, the external ports being rotatable around the axis relative to the plurality of chambers to place the external ports selectively in fluidic communication with the plurality of chambers, and wherein the crossover channel comprises a crossover groove on the external port surface.

117. The system of claim 116 wherein the external ports are disposed within a range of external port radii from the axis and the crossover groove is disposed within a range of crossover groove radii from the axis, the range of external port radii and the range of crossover groove radii being non-overlapping.

118. The system of claim 117 wherein the crossover groove is a circular arc lying on a common crossover groove radius from the axis.

119. The system of claim 117 wherein the external ports are spaced from the axis by a common radius.

120. The system of claim 97 wherein the external ports are disposed on an external port surface that is generally conical relative to the axis of rotation of the body, the external ports including a first external port angularly spaced from a second external port about the axis.

121. The system of claim 120 wherein the first external port lies on a first transverse plane which is perpendicular to the axis and which is longitudinally offset in the direction of the axis from a second transverse plane which is perpendicular to the axis, wherein the second external port lies on the second plane.

122. The system of claim 121 wherein the body includes a crossover groove disposed on the external port surface.

123. The system of claim 122 wherein the crossover groove extends longitudinally between the first transverse plane and the second transverse plane.

124. The system of claim 97 wherein the fluid sample processing region comprises an active member selected from the group consisting of a microfluidic chip, a solid phase material, a filter, a filter stack, an affinity matrix, a magnetic separation matrix, a size exclusion column, and a capillary tube.

125. The system of claim 97 wherein at least two of the plurality of chambers are separated by a flexible wall to permit change-over of chamber volumes between the chambers.

126. The system of claim 97 wherein the plurality of chambers comprise a side chamber including an inlet port, an outlet port, and a filter disposed at the inlet port.

* * * * *